(12) United States Patent
Azar et al.

(10) Patent No.: US 7,897,581 B2
(45) Date of Patent: Mar. 1, 2011

(54) METHODS AND COMPOUNDS FOR PROMOTING VESSEL REGRESSION

(75) Inventors: Dimitri T. Azar, Brookline, MA (US); Elena Albé, Milan (IT); Jin-Hong Chang, Brookline, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 286 days.

(21) Appl. No.: 11/363,402

(22) Filed: Feb. 24, 2006

(65) Prior Publication Data
US 2006/0211057 A1 Sep. 21, 2006

Related U.S. Application Data

(60) Provisional application No. 60/656,168, filed on Feb. 24, 2005, provisional application No. 60/719,998, filed on Sep. 23, 2005.

(51) Int. Cl.
*A61K 48/00* (2006.01)
*C07H 21/04* (2006.01)
(52) U.S. Cl. ........................................ 514/44; 536/23.1
(58) Field of Classification Search ........................ None
See application file for complete search history.

(56) References Cited

U.S. PATENT DOCUMENTS

| | | | |
|---|---|---|---|
| 6,692,925 B1 | 2/2004 | Miyazono et al. | |
| 2003/0152926 A1* | 8/2003 | Murray et al. | 435/6 |
| 2008/0175844 A1* | 7/2008 | Grinberg et al. | 424/139.1 |

OTHER PUBLICATIONS

Alexander et al., "Tumor-specific expression and alternate splicing of messenger ribonucleic acid encoding activin/transforming growth factor-beta receptors in human pituitary adenomas" J. Clin. Endocrinol. Metab. 81:783-790 (1996).
Bischoff et al., "Scanning electron microscopic studies of the hyaloid vascular system in newborn mice exposed to O2 and CO2" Graefes Arch. Clin. Exp. Ophthalmol. 220(6):257-263 (1983).
Brant et al., "Ocular manifestations in hereditary hemorrhagic telangiectasia (Rendu-Osler-Weber disease)" Am. J. Ophthalmol. 107:642-646 (1989).
Chang et al., "Corneal neovascularization" Curr. Opin. Ophthalmol. 12:242-249 (2001).
Chang et al., "Functional characterization of neostatins, the MMP-derived, enzymatic cleavage products of type XVIII collagen" FEBS Lett. 579:3601-3606 (2005).
Coffin et al., "ALK1 and p80 expression and chromosomal rearrangements involving 2p23 in inflammatory myofibroblastic tumor" Mod. Pathol. 14:569-576 (2001).
Dawson et al., "Pigment epithelium-derived factor: a potent inhibitor of angiogenesis" Science 285:245-248 (1999).
Diez-Roux et al.," Macrophages induce apoptosis in normal cells in vivo" Development 124(18):3633-3638 (1997).
Feeney et al., "Role of vascular endothelial growth factor and placental growth factors during retinal vascular development and hyaloid regression" Invest. Ophthalmol. Vis. Sci. 44 (2):839-847 (2003).
Felton et al., "Vitreous inhibition of tumor neovascularization" Arch. Ophthalmol. 97(9):1710-1713 (1979).
Feng et al., "Specificity and versatility in TGF-beta signaling through Smads" Annu. Rev. Cell. Dev. Biol. 659-693 (2005).
Gabison et al., "Anti-angiogenic role of angiostatin during corneal wound healing" Exp. Eye. Res. 78:579-589 (2004).
GenBank Accession No. NM_000020.1.
GenBank Accession No. NP_000011.1.
Goumans et al., "Functional analysis of the TGFbeta receptor/Smad pathway through gene ablation in mice" Int. J. Dev. Biol. 44:253-265 (2000).
Goumans et al., "Balancing the activation state of the endothelium via two distinct TGF-beta type I receptors" EMBO J. 21:1743-1753 (2002).
Goumans et al., "Controlling the angiogenic switch: a balance between two distinct TGF-b receptor signaling pathways" Trends. Cardiovasc. Med. 13:301-307 (2003).
Ito et al., "Regression of the hyaloid vessels and pupillary membrane of the mouse" Anat. Embryol. (Berl). 200(4):403-411 (1999).
Jack, "Regression of the hyaloid vascular system. An ultrastructural analysis" Am. J. Ophthalmol. 74 (2):261-272 (1972).
Johnson et al., "Mutations in the activin receptor-like kinase 1 gene in hereditary haemorrhagic telangiectasia type 2" Nat. Genet. 13:189-195 (1996).
Lamouille et al., "Activin receptor-like kinase 1 is implicated in the maturation phase of angiogenesis" Blood 100:4495-4501 (2002).
Lang et al., "Macrophages are required for cell death and tissue remodeling in the developing mouse eye" Cell 74 (3):453-462 (1993).
Lang et al., "Apoptosis during macrophage-dependent ocular tissue remodeling" Development 120(12):3395-3403 (1994).
Latker et al., "Regression of the tunica vasculosa lentis in the postnatal rat" Invest. Ophthalmol. Vis. Sci. 21(5):689-699 (1981).
Lebrin et al., "TGF-beta receptor function in the endothelium" Cardiovasc. Res. 65:599-608 (2005).
Lebrin et al., "Endoglin promotes endothelial cell proliferation and TGF-beta/ALK1 signal transduction." EMBO J. 23:4018-4028 (2004).
Lutty et al., "Vitreous: an inhibitor of retinal extract-induced neovascularization" Invest. Ophthalmol. Vis. Sci. 24 (1):52-56 (1983).
Lutty et al., "Heterogeneity in localization of isoforms of TGF-beta in human retina, vitreous, and choroid" Invest. Ophthalmol. Vis. Sci. 34 (3):477-487 (1993).
Mahmoud et al., "Intraoperative choroidal hemorrhage in the Osler-Rendu-Weber syndrome" Am. J. Ophthalmol. 133:282-284 (2002).
Mann The Development of the Human Eye. pp. 201-232. Grune & Stratton Inc: New York (1964).

(Continued)

*Primary Examiner* — Ruixiang Li
(74) *Attorney, Agent, or Firm* — Fish & Richardson P.C.

(57) ABSTRACT

The present invention relates, at least in part, to methods and compositions for treating and diagnosing disorders associated with neovascularization, and methods for identifying targets and compositions used in treating and diagnosing such disorders.

16 Claims, 4 Drawing Sheets

OTHER PUBLICATIONS

McAllister et al., "Endoglin, a TGF-beta binding protein of endothelial cells, is the gene for hereditary haemorrhagic telangiectasia type 1" Nat. Genet. 8:345-351 (1994).

McMenamin et al., "Characterization of the macrophages associated with the tunica vasculosa lentis of the rat eye" Invest. Ophthalmol. Vis Sci. 43 (7):2076-2082 (2002).

Meeson et al., "A relationship between apoptosis and flow during programmed capillary regression is revealed by vital analysis" Development 122(12):3929-3838 (1996).

Mitchell et al., "Regression of vessels in the tunica vasculosa lentis is initiated by coordinated endothelial apoptosis: a role for vascular endothelial growth factor as a survival factor for endothelium" Dev. Dyn. 213(3):322-333 (1998).

Murthy et al., "Corneal transduction to inhibit angiogenesis and graft failure" Invest. Ophthalmol. Vis. Sci. 44:1837-1842 (2003).

Oh et al., "Activin receptor-like kinase 1 modulates transforming growth factor-beta 1 signaling in the regulation of angiogenesis" Proc Natl Acad Sci USA 97:2626-2631 (2000).

Panchenko et al., "Type I receptor serine-threonine kinase preferentially expressed in pulmonary blood vessels" Am. J. Physiol. 270:L547-L558 (1996).

Pepper, "Transforming growth factor-beta: vasculogenesis, angiogenesis, and vessel wall integrity" Cytokine Growth Factor. Rev. 8:21-43 (1997).

Preis et al., "Inhibition of neovascularization by an extract derived from vitreous" Am. J. Ophthalmol. 84(3):323-328 (1977).

Pulford et al., "Detection of anaplastic lymphoma kinase (ALK) and nucleolar protein nucleophosmin (NPM)-ALK proteins in normal and neoplastic cells with the monoclonal antibody ALK1" Blood 89:1394-1404 (1997).

Ramesh et al., "Immunolocalisation of opticin in the human eye" Br. J. Ophthalmol. 88(5):697-702 (2004).

Roman et al., "Disruption of acvrl1 increases endothelial cell number in zebrafish cranial vessels" Development 129:3009-3019 (2002).

Sadahira et al., "Bone marrow involvement in NPM-ALK-positive lymphoma: report of two cases" Pathol. Res. Pract. 195:657-661 (1999).

Seki et al., "Arterial endothelium-specific activin receptor-like kinase 1 expression suggests its role in arterialization and vascular remodeling" Circ. Res. 93:682-689 (2003).

Smith, "Systematic evaluation of the Mouse Eye: Anatomy, Pathology, and Biomethods" 45-63 Sunders (2002).

Srinivasan et al., "A mouse model for hereditary hemorrhagic telangiectasia (HHT) type 2" Hum. Mol. Genet. 12:473-482 (2003).

Taylor et al., "Partial purification of a 5.7K glycoprotein from bovine vitreous which inhibits both angiogenesis and collagenase activity" Biochem. Biophys. Res. Commun. 133 (3):911-916 (1985).

ten Dijke et al., "Characterization of type I receptors for transforming growth factor-beta and activin" Science 264:101-104 (1994).

Urness et al., "Arteriovenous malformations in mice lacking activin receptor-like kinase-1" Nat. Genet. 26:328-331 (2000).

Vase et al., "Ocular lesions in hereditary haemorrhagic telangiectasia" Acta. Ophthalmol. Copen. 57:1084-1090 (1979).

Zhu et al., "Effect of human vitreous and hyalocyte-derived factors on vascular endothelial cell growth" Aust. N. Z. J. Ophthalmol. 25(Suppl.)1:S57-S60 (1997).

* cited by examiner

Figure 1A-C
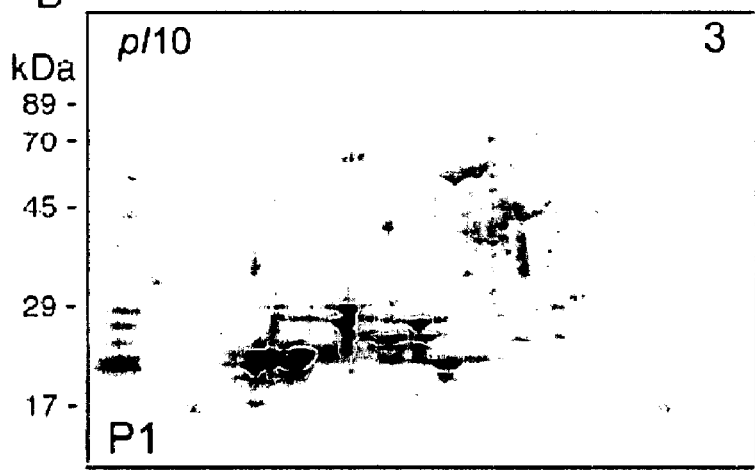
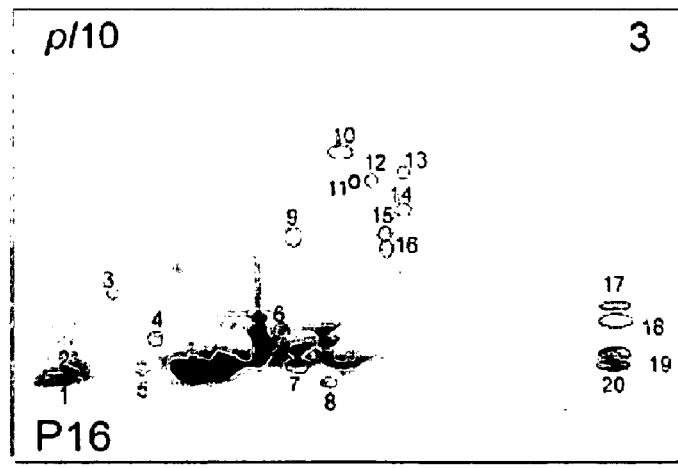

Figure 2A-Q
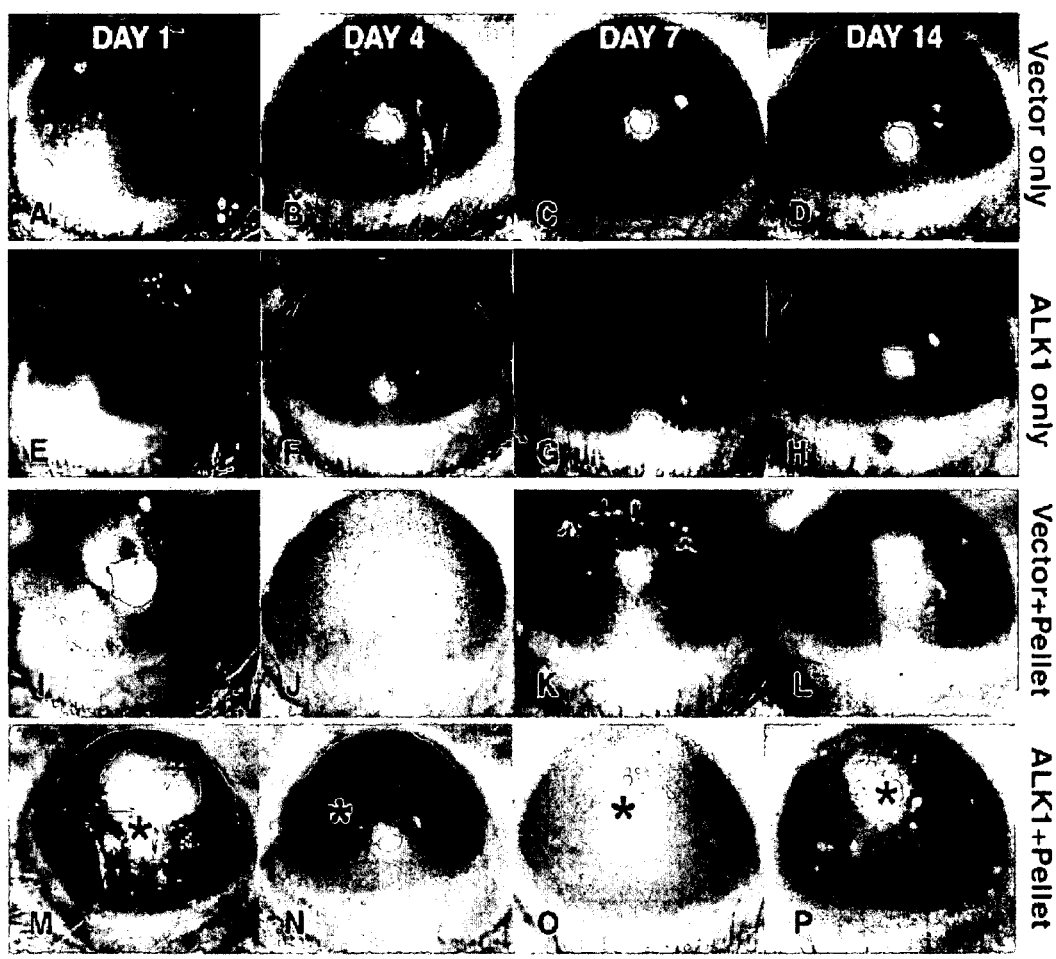
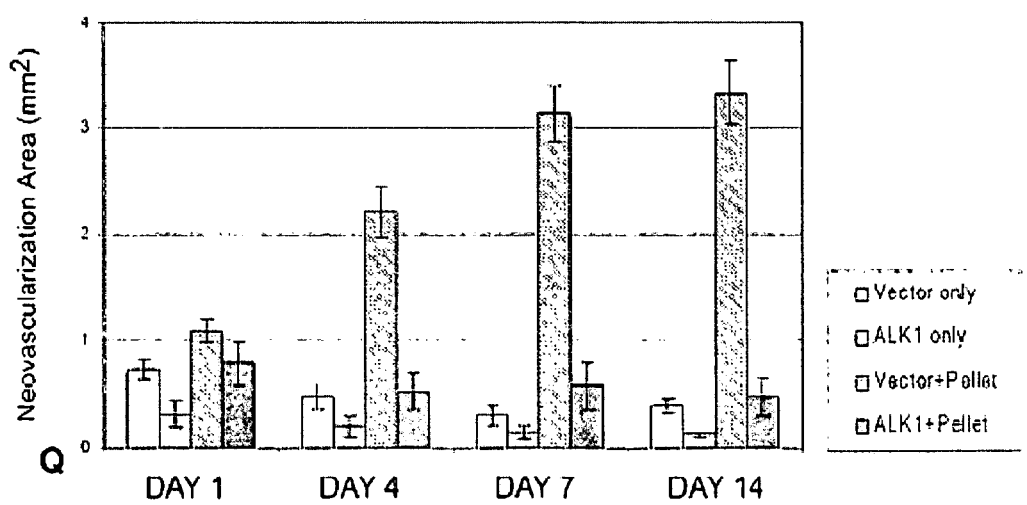

Figure 3A

```
LOCUS       NM_000020               1970 bp    mRNA    linear   PRI 19-
JUL-2005
DEFINITION  Homo sapiens activin A receptor type II-like 1 (ACVRL1),
mRNA.
ACCESSION   NM_000020
VERSION     NM_000020.1  GI:4557242
KEYWORDS    .
SOURCE      Homo sapiens (human)
FEATURES             Location/Qualifiers
source1..1970
  /organism="Homo sapiens"
  /mol_type="mRNA"
  /db_xref="taxon:9606"
  /chromosome="12"
  /map="12q11-q14"
gene   1..1970
  /gene="ACVRL1"
  /note="synonyms: HHT, ALK1, HHT2, ORW2, SKR3, ALK-1, ACVRLK1"
  /db_xref="GeneID:94"
  /db_xref="HPRD:HPRD_03181"
  /db_xref="MIM:601284"
CDS    283..1794
  /gene="ACVRL1"
  /EC_number="2.7.1.37"
  /codon_start=1
  /product="activin A receptor type II-like 1"
  /protein_id="NP_000011.1"
  /db_xref="GI:4557243"
  /db_xref="GeneID:94"
  /db_xref="HPRD:HPRD_03181"
  /db_xref="MIM:601284"
  /translation="MTLGSPRKGLLMLLMALVTQGDPVKPSRGPLVTCTCESPHCKGP
TCRGAWCTVVLVREEGRHPQEHRGCGNLHRELCRGRPTEFVNHYCCDSHLCNHNVSLV
LEATQPPSEQPGTDGQLALILGPVLALLALVALGVLGLWHVRRRQEKQRGLHSELGES
SLILKASEQGDTMLGDLLDSDCTTGSGSGLPFLVQRTVARQVALVECVGKGRYGEVWR
GLWHGESVAVKIFSSRDEQSWFRETEIYNTVLLRHDNILGFIASDMTSRNSSTQLWLI
THYHEHGSLYDFLQRQTLEPHLALRLAVSAACGLAHLHVEIFGTQGKPAIAHRDFKSR
NVLVKSNLQCCIADLGLAVMHSQGSDYLDIGNNPRVGTKRYMAPEVLDEQIRTDCFES
YKWTDIWAFGLVLWEIARRTIVNGIVEDYRPPFYDVVPNDPSFEDMKKVVCVDQQTPT
IPNRLAADPVLSGLAQMMRECWYPNPSARLTALRIKKTLQKISNSPEKPKVIQ"
[SEQ ID NO:1]
```

Figure 3B

```
sig_peptide     283..345
                /gene="ACVRL1"
mat_peptide     346..1791
                /gene="ACVRL1"
                /product="activin A receptor type II-like 1 mature
                peptide"
misc_feature    346..636
                /gene="ACVRL1"
                /note="encoding predicted extracellular domain"
misc_feature    382..567
                /gene="ACVRL1"
                /note="encoding cysteine-rich domain"
misc_feature    637..705
                /gene="ACVRL1"
                /note="encoding predicted transmembrane domain"
misc_feature    706..1791
                /gene="ACVRL1"
                /note="encoding predicted intracellular domain"
misc_feature    892..1767
                /gene="ACVRL1"
                /note="encoding predicted serine/threonine kinase domain"
ORIGIN
    1 aggaaacggt ttattaggag ggagtggtgg agctgggcca ggcaggaaga cgctggaata
   61 agaaacattt ttgctccagc ccccatccca gtcccgggag gctgccgcgc cagctgcgcc
  121 gagcgagccc ctccccggct ccagcccggt ccggggccgc gccggacccc agcccgccgt
  181 ccagcgctgg cggtgcaact gcggccgcgc ggtggagggg aggtggcccc ggtccgccga
  241 aggctagcgc cccgccaccc gcagagcggg cccagaggga ccatgacctt gggctccccc
  301 aggaaaggcc ttctgatgct gctgatggcc ttggtgaccc agggagaccc tgtgaagccg
  361 tctcggggcc cgctggtgac ctgcacgtgt gagagcccac attgcaaggg gcctacctgc
  421 cggggggcct ggtgcacagt agtgctggtg cgggaggagg ggaggcaccc caggaacat
  481 cggggctgcg ggaacttgca cagggagctc tgcaggggc gccccaccga gttcgtcaac
  541 cactactgct gcgacagcca cctctgcaac cacaacgtgt ccctggtgct ggaggccacc
  601 caacctcctt cggagcagcc gggaacagat ggccagctgg ccctgatcct gggccccgtg
  661 ctggccttgc tggccctggt ggccctgggt gtcctgggcc tgtggcatgt ccgacggagg
  721 caggagaagc agcgtggcct gcacagcgag ctgggagagt ccagtctcat cctgaaagca
  781 tctgagcagg gcgacacgat gttggggac ctcctggaca gtgactgcac cacagggagt
  841 ggctcagggc tccccttcct ggtgcagagg acagtggcac ggcaggttgc cttggtggag
  901 tgtgtgggaa aaggccgcta tggcgaagtg tggcgggct tgtggcacgg tgagagtgtg
  961 gccgtcaaga tcttctcctc gagggatgaa cagtcctggt tccgggagac tgagatctat
 1021 aacacagtat tgctcagaca cgacaacatc ctaggcttca tcgcctcaga catgacctcc
 1081 cgcaactcga gcacgcagct gtggctcatc acgcactacc acgagcacgg ctccctctac
 1141 gactttctgc agagacagac gctggagccc atctggctc tgaggctagc tgtgtccgcg
 1201 gcatgcggcc tggcgcacct gcacgtggag atcttcggta cacagggcaa accagccatt
 1261 gcccaccgcg acttcaagag ccgcaatgtg ctggtcaaga gcaacctgca gtgttgcatc
 1321 gccgacctgg gctggctgt gatgcactca cagggcagcg attacctgga tcggcaac
 1381 aacccgagag tgggcaccaa gcggtacatg gcacccgagg tgctggacga gcagatccgc
 1441 acggactgct ttgagtccta caagtggact gacatctggg cctttggcct ggtgctgtgg
 1501 gagattgccc gccggaccat cgtgaatggc atcgtggagg actatagacc acccttctat
 1561 gatgtggtgc ccaatgaccc cagctttgag gacatgaaga aggtggtgtg tgtggatcag
 1621 cagacccca ccatccctaa ccggctggct gcagacccgg tcctctcagg cctagctcag
 1681 atgatgcggg agtgctggta cccaaaccc tctgcccgac tcaccgcgct gcggatcaag
 1741 aagacactac aaaaaattag caacagtcca gagaagccta aagtgattca atagcccagg
 1801 agcacctgat tcctttctgc ctgcaggggg ctgggggggt ggggggcagt ggatggtgcc
 1861 ctatctgggt agaggtagtg tgagtgtggt gtgtgctggg gatgggcagc tgcgcctgcc
 1921 tgctcggccc ccagcccacc cagccaaaaa tacagctggg ctgaaacctg
[SEQ ID NO:2]
21262278.doc
```

METHODS AND COMPOUNDS FOR PROMOTING VESSEL REGRESSION

CLAIM OF PRIORITY

This application claims the benefit under 35 USC §119(e) of U.S. Provisional Patent Applications Ser. Nos. 60/656,168, filed on Feb. 24, 2005, and 60/719,998, filed on Sep. 23, 2005. The entire contents of both applications are hereby incorporated by reference.

TECHNICAL FIELD

This invention relates to methods and compounds for promoting vessel regression, e.g., to treat disorders associated with neovascularization.

BACKGROUND

The hyaloid vascular system (HVS) is a transiently existing network of capillaries that function to nourish the immature lens and primary vitreous of the developing eye. The hyaloid artery (HA) runs from the back of the eye to the embryonic lens giving rise to a capillary plexus that surrounds the lens, consisting of the vasa hyaloidea propria (VHP), the tunica vasculosa lentis (TVL) and the pupillary membrane (PM). The HVS provides a useful system to investigate physiologically relevant angiogenesis and vascular remodeling processes.

The first elements of the human hyaloid vasculature to undergo regression are the VHP, followed by the TVL, PM and lastly the main hyaloid trunk, commencing at 12 weeks of gestation (WG) and culminating in the involution of the entire hyaloid by 35-36 WG (Mann I. The Development of the Human Eye. Pp 201-32. Grune & Stratton Inc: New York, 1964.). In humans, failure of the hyaloid vascular system to regress can lead to a condition known as persistent hyperplastic primary vitreous (PHPV), which can result in permanent blindness if left untreated.

Mitchell and coworkers showed that in mice the hyaloid vascular system is first recognized at embryonic day 10.5 (E10.5), is complete by E13.5 and regresses postnatally prior to eyelid opening (Mitchell C A, et al., Dev. Dyn. 213(3):322-33 (1998)). During mouse development, the longer branches of the TVL and the longer hyaloid vessels are removed by post-gestational day 16 (P16) (Mitchell C A, et al., Dev. Dyn. 213(3):322-33 (1998)). Ito et al. presented partially similar results, showing that the PM had completely disappeared by P16, and the VHP had disappeared between P12 and P16, but the TVL and the hyaloid artery remained even at P16 (Ito and Yoshioka, Anat. Embryol. (Berl). 200(4):403-11 (1999)). Smith showed a gradual disappearance of the TVL and hyaloid artery from P14 to P30 (Smith, Systematic evaluation of the Mouse Eye: Anatomy, Pathology, and Biomethods. Pp 45-63. Sunders, 2002.).

Previous hypotheses of the mechanism of regression of the hyaloid vascular system included the following:

A. The reduction or the cessation of the blood flow into the HVS was thought to be one of the major triggering factors of the regression in these vessels. A change in the blood flow distribution (Bischoff et al., Graefes Arch. Clin. Exp. Ophthalmol. 220 (6):257-63 (1983)) and competition between the blood vessels in the retina and the lens for the blood flow can lead to the degeneration of the HVS when the retinal blood vessels become larger and require more nutrients.

B. Vascular obstruction, physical vascular stretching, localized circulatory stasis, and arterial vasoconstriction were regarded as triggering factors of the regression of the HVS (Jack, Am. J. Ophthalmol. 74 (2):261-72 (1972); Latker and Kuwabara, Invest. Ophthalmol. Vis. Sci. 21 (5):689-99 (1981)). The regression occurs first in those vessels that were hemodynamically disadvantaged and consequently had less blood flow.

C. Meeson et al. have shown that the occurrence of apoptosis in the PM strictly correlated to the flow status; as the flow decreased the appearance of apoptosis in capillaries increased (Meeson et al., Development. 122(12):3929-38 (1996)). The same correlation may exist in the hyaloid vascular system. As the main role of the HVS is supposed to be to nourish the retina before the maturation of retinal vessels, the HVS may regress after the completion of these vessels.

D. Macrophages may also be required in the programmed regression of the PM and the HVS (Lang and Bishop, Cell. 13; 74 (3):453-62 (1993); Lang et al., Development. 120 (12):3395-403 (1994); Diez-Roux and Lang, Development. 124 (18):3633-8 (1997)).

E. The anti-angiogenic ability of the vitreous humor and vitreous extracts may also be important in the regression of the TVL (Preis et al., Am. J. Ophthalmol. 84 (3):323-8 (1977); Felton et al., Arch. Ophthalmol. 97 (9):1710-3 (1979); Lutty et al., Invest. Ophthalmol. Vis. Sci. 24 (1):52-6 (1983); Taylor and Weiss, Biochem Biophys Res Commun. 133 (3):911-6 (1985); Zhu et al., Aust. N. Z. J. Ophthalmol. 25 Suppl 1:S57-60 (1997); Ramesh et al., Br. J. Ophthalmol. 88 (5):697-702 (2004)). Hyalocytes play also a role in the regression of the TVL (McMenamin et al., Invest. Ophthalmol. Vis Sci. 43 (7):2076-82 (2002)). Lutty et al. have demonstrated that the hyalocytes produce and process transforming growth factor-β (TGF-β) which may inhibit is the proliferation of the vascular endothelial cells in this system (Lutty et al., Invest. Ophthalmol. Vis. Sci. 34 (3):477-87 (1993)).

F. Several survival factors may protect cells from apoptosis, including fibroblast growth factor (FGF), platelet-derived growth factor (PDGF) and vascular endothelial growth factor (VEGF). A reduction in levels of these growth factors below a critical threshold may lead to the induction of an apoptotic program.

The role of VEGF in the maintenance of the VHP is not clear. Feenay et al. demonstrated that the TVL degeneration was unexpectedly uninfluenced by treatment with a VEGF A antibody, suggesting that programmed regression is independent of VEGF A, or that the development and maturation of the lens had gone beyond the point of the plasticity and susceptibility to certain growth factors (Feeney et al., Invest. Ophthalmol. Vis. Sci. 44 (2):839-47 (2003)).

SUMMARY

The present invention is based, at least in part, on the results of proteomic analysis of the mouse lens and vitreous during postnatal development, which identified novel proteins that contribute to regression of the hyaloid system. Among other proteins, two-dimensional electrophoresis and mass spectrometry of the developing mouse lens and vitreous identified activin receptor-like kinase-1 (ALK1) as a differentially expressed protein during HVS regression; immunohistochemical staining demonstrated the localization of ALK1 in the TVL; and overexpression of ALK1 in the cornea resulted in inhibition of bFGF-induced corneal neovascularization in vivo. Activin receptor-like kinase-1 (ALK1) activates Smads1, 5 and 8 which down-regulate VEGF production. In contrast, ALK5 activates Smads2 and 3 which up-regulate VEGF production (Goumans et al., EMBO. J. 21, 1743-1753

(2002)). Expression of ALK1 in blood vessels and mutations of the ALK1 gene in patients with human type II hereditary hemorrhagic telangiectasia, a multi-systemic vascular dysplasia, suggests that ALK1 may play an important role during normal vascular development (Oh et al., Proc Natl Acad Sci USA 97, 2626-2631 (2000)).

Thus, ALK1 polypeptides and nucleic acids are useful compositions and targets for treating disorders associated with neovascularization (NV), and in cancer therapy.

In one aspect, the invention provides methods for treating patients who have a disorder associated with neovascularization, e.g., an ophthalmological disorder associated with neovascularization. The methods include administering to the patient a therapeutically effective amount of an ALK1 polypeptide or nucleic acid composition, e.g., as described herein. The invention further includes therapeutic compositions including the ALK1 polypeptides or nucleic acids described herein, as well as inhibitors and/or agonists thereof, and methods for identifying such compounds.

Ophthalmological disorders associated with neovascularization include eye cancer, age-related macular degeneration, retinopathy of prematurity, corneal graft rejection, glaucoma, diabetic retinopathy, wounds, age-related macular degeneration, herpetic and infectious keratitis, ocular ischemia, neovascular glaucoma, corneal, uveal and iris neovascularization, orbital and eyelid tumors, Stevens Johnson Syndrome, ocular cicatricial pemphigoid, and ocular surface diseases. In some embodiments, the ophthalmological disorder is associated with corneal, retinal, choroidal, uveal, or iris neovascularization. For an ophthalmological disorder, the administering can be, e.g., topical or parenteral administration into the eye, e.g., including, but not limited to, local injection into or near the cornea, retina, vitreous, uvea, orbit, eyelid, conjunctiva, or iris.

In some embodiments, the disorder is cancer, e.g., as described herein.

In some embodiments, the subject is selected on the basis that he or she has a disorder associated with neovascularization as described herein.

In some embodiments, the administering can be, e.g., local or systemic, e.g., parenteral or oral.

In another aspect, the invention provides methods for identifying candidate therapeutic compounds for the treatment of a disorder associated with neovascularization. The methods include obtaining a sample including a cell that is capable of expressing one or more of the genes listed in Tables 1-6; contacting the sample with the test compound; and evaluating levels, expression, or activity of the gene(s) in the sample, e.g., in the cell. Modulation of levels, expression, or activity of the gene(s) in the sample indicates that the test compound is a candidate therapeutic compound for the treatment of a disorder associated with neovascularization. The levels, expression, or activity of the gene in the sample can be evaluated by methods known in the art, e.g., enzyme assays, immunoassays, high-throughput DNA, RNA, or protein assays, etc. In some embodiments, the gene is ALK1.

In some embodiments, the method further includes administering the candidate therapeutic compound to an animal model of a disorder associated with neovascularization, and monitoring the animal model for an effect of the candidate therapeutic compound on a parameter of the disorder, e.g., vascularisation, in the animal. A candidate therapeutic compound that causes an improvement in the parameter in the animal model is a candidate therapeutic agent for the treatment of the disorder. In some embodiments, the methods further include administering the candidate therapeutic agent to a subject having the disorder, e.g., a subject in a clinical trial, and monitoring a parameter of the disorder in the subject. A candidate therapeutic agent that improves the parameter in the subject is a therapeutic agent for the treatment of the disorder. In some embodiments, the parameter is visual acuity. In some embodiments, the methods include administering a therapeutically effective amount of the therapeutic agent to a subject in need of treatment for the disorder, thereby treating the disorder.

In a further aspect, the invention provides methods for identifying candidate compounds, e.g., naturally-occurring compounds, e.g., a polypeptide or biologically active fragment thereof, for the treatment of a disorder associated with neovascularization. The methods include providing a sample including:

(i) cells from a subject, e.g., a human subject, having a disorder associated with blood vessel regression, e.g., retinopathy of prematurity, persistent hyperplastic primary vitreous (PHPV), or retrolental fibroplasia; or (ii) cells from a subject, e.g., a human subject, in a stage of development that is associated with vessel regression, e.g., a stage in the development of the hyaloid vascular system;

determining the expression levels of proteins, e.g., one or more, e.g., 2, 3, 5, 10, 15, 20, 25, 30, 50 or 100, of the of the proteins listed in Tables 1-6, in the sample; and comparing the expression levels to a reference, e.g., a sample from an unaffected subject or a subject at a different stage of development associated with blood vessel regression, e.g., a different stage the development of the hyaloid vascular system. A compound that is differentially expressed, e.g., significantly differentially expressed, is a candidate compound for the treatment of a disorder associated with neovascularization.

In another aspect, the invention includes methods for treating a disorder associated with neovascularization, e.g., an ophthalmological disorder associated with neovascularization as described herein, in a subject by administering a therapeutically effective amount of a therapeutic composition including an activin receptor-like kinase-1 (ALK1) polynucleotide or polypeptide, or an active fragment thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIGS. 1A-C. Proteomic analysis of proteins from the lens and vitreous of P1 and P16 mice. The merged image (1A) represents the warped image between P1 (1B) and P16 (1C) obtained with Phoretix 2D evolution software. The proteins excised from 2-D gel (P16) for analysis and identification by mass spectrometry are identified with numbers 1-20 (1C).

FIGS. 2A-Q. bFGF-pellet induced corneal neovascularization (NV) is inhibited by naked ALK1 DNA injection in vivo. No-pellet controls are shown in 3A-H: Injection of naked DNA [ALK1 (2E-H) and vector only (2A-D)] did not induce corneal NV. The vector plus pellet positive controls are shown in 31-L: development of NV in the corneal stroma was evident by day 4 (2J); new vessels continued to grow in the direction of the pellet on days 7 and 14. None of the mice in the ALK1 and pellet groups (2M-P) showed development of corneal NV on days 1, 4, 7, and 14 after pellet implantation. Asterisk (*) indicates pellet implantation. The area of corneal NV of the four groups at days 1-14 is shown (2Q).

FIG. 3A-B are the amino acid (3A; SEQ ID NO:1) and nucleic acid (3B; SEQ ID NO:2) sequences of human ALK1.

DETAILED DESCRIPTION

A proteomic approach was used to decipher the biochemical events coexistent with the time points of the progressive regression of the HVS. Reproducible two-dimensional electrophoresis (2-DE) maps were used to study modifications of the protein expression profiles occurring in the mouse lens and vitreous at various stages of the regression of the hyaloid capillaries network. The identity of separated and differentially expressed proteins was confirmed by mass spectrometry (Thermo Electron's Finnigan LCQ Deca XP Plus™ Electrospray ionization (ESI) mass spectrometer).

In particular, attention was focused on the differential protein expression between postnatal day 1 and postnatal day 16. Optical microscopy and hematoxylin-eosin staining studies showed the progressive regression of the hyaloid vascular system of the mouse eye between P1, in which PM, TVL and HV are present and P16, in which these mature capillary structures[21] are almost completely regressed. Proteins identified in these screens are targets for therapeutic intervention for the treatment of various disorders associated with neovascularization. Tables 1-6 list proteins which are expected to play a role in vascularisation, inhibition of blood vessel regression, both in the HVS and in other systems, e.g., including pathophysiological processes, and are thus useful in the treatment of disorders associated with neovascularization, as described herein.

Activin Receptor-Like Kinase-1 (ALK1)

TGF-β is a potent inhibitor of vascular endothelial cell proliferation (Lutty et al., (1993), supra). It regulates endothelial proliferation via two receptor/Smad (mother against decapentaplegic) pathways. After ligand binding and activation of Type I receptors, signals are transduced from the membrane to the nucleus via Smads (Seki et al., Circ Res 93, 682-689 (2003)). Type I receptors recruit and phosphorylate Smads, such as Smads2 and 3 by the TβRI/ALK5 type I receptor in response to TGF-β, and Smads1, 5 and 8 by the BMP (bone morphogenetic protein) type I receptors (Feng, Ann. Rev. Cell. Dev. Biol. 659-693 (2005)).

ALK1 is one of the seven Type I receptors for the TGF-β family of proteins (ten Dijke et al., Science 264, 101-104 (1994); GeneID: 94; GenBank Accession Nos. NM_000020.1 (nucleic acid) and NP_000011.1 (polypeptide)). ALK1 expression has been detected in endothelial cells of highly vascularized tissues (lungs and placenta) (Panchenko et al., Am. J. Physiol. 270, L547-L558 (1996)), normal and neoplastic pituitary cells (Alexander et al., J. Clin. Endocrinol. Metab. 81, 783-790 (1996)), anaplastic large cell lymphoma (Sadahira et al., Pathol. Res. Pract. 195, 657-661 (1999)), inflammatory myofibroblastic tumor (Coffin et al., Mod. Pathol. 14, 569-576 (2001)) and central nervous system cells (Pulford et al., Blood 89, 1394-1404 (1997)). ALK1 transduces the TGF-β signal by phosphorylating Smald1, Smad5 or Smad8 (Goumans, et al., EMBO. J. 21, 1743-1753 (2002); Oh et al., Proc. Natl. Acad. Sci. U.S.A. 97, 2626-2631 (2000)). In contrast, ALK5 activates Smads2 and 3 which up-regulate VEGF production (Goumans et al., EMBO J 21, 1743-1753 (2002)). Upon phosphorylation by the receptors, Smad complexes translocate into the nucleus, where they cooperate with sequence-specific transcription factors at the promoter DNA to regulate gene expression (Feng and Derynck, Annu. Rev. Cell. Dev. Biol. 659-693 (2005)). This functional and physical interaction confer both specificity and complexity in transcriptional responses to TGF-β family ligands (Id.).

Mutations of the ALK1 or endoglin genes have been linked to the human vascular disorder Hereditary Hemorrhagic Telangiectasia (HHT) (Johnson et al., Nat. Genet. 13, 189-195 (1996); McAllister et al., Nat. Genet. 8, 345-351 (1994)). This is an autosomal-dominant disorder, also known as Osler-Rendu-Weber syndrome, characterized by the age-dependent development of focal arteriovenous malformations and telangiectases (Srinivasan et al., Hum. Mol. Genet. 12, 473-482 (2003)). HHT type 2 is caused by loss of function of the activin receptor-like kinase I (ACVRL1 or ALK1) (Id.). The disease is characterized by dilated, thin-walled, vascular anomalies of the skin and mucous membranes and recurrent epistaxis. In the literature, abnormal eye disorders have been documented in 45-65% of patients with HHT, with the most common lesions being conjunctival telangiectasias (Brant et al., Am. J. Ophthalmol. 107, 642-646 (1989); Vase and Vase, Acta. Ophthalmol. Copen. 57, 1084-1090 (1979)). Retinal arteriovenous malformations, retinal telangiectasia and choroidal haemorrhage during intraocular surgery have also been noted (Brant et al., (1989) supra; Mahmoud et al., Am. J. Ophthalmol. 133, 282-284 (2002)).

The sequences of the human ALK1 polypeptide (SEQ ID NO:1) and polynucleotide (SEQ ID NO:2) are shown in FIG. 3. Active fragments thereof include, e.g., amino acids 22-503 of SEQ ID NO:1, or nucleotides 346-1791 of SEQ ID NO:2. Active fragments can also include the GS motif, i.e., amino acids 173-202 of SEQ ID NO:1; the Serine/Threonine protein kinases, catalytic domain, i.e., amino acids 204-487 of SEQ ID NO:1; and/or the Activin types I and II receptor domain, i.e., amino acids 19-103 of SEQ ID NO:1. An active fragment retains the ability to block bFGF-induced neovascularization. Homologs of the human ALK1 in other species are known, e.g., for rat, GenBank Accession No. NM_022441.1; for mouse, NM_009612.1

Pharmaceutical Compositions and Methods of Administration

The polypeptides listed in Tables 1-6, and nucleic acid molecules encoding or inhibiting them, can be incorporated into pharmaceutical compositions as active ingredients. In some embodiments, the pharmaceutical compositions include a human ALK1 polypeptide (e.g., SEQ ID NO:1) or polynucleotide (e.g., SEQ ID NO:2), or an active fragment thereof. In general, it will be preferable to match the composition to the species that is being treated; thus, for example, when treating experimental animals such as mice other species can be used, e.g., from rats or mice.

Pharmaceutical compositions typically include the active ingredient and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is typically formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

In some embodiments, the composition is especially adapted for administration into or around the eye. For example, a composition can be adapted to be used as eye drops, or injected into the eye, e.g., using peribulbar or intravitreal injection. Such compositions should be sterile and substantially endotoxin-free, and within an acceptable range of pH. Certain preservatives are thought not to be good for the eye, so that in some embodiments a non-preserved formulation is used. Formulation of eye medications is known in the art, see, e.g., *Ocular Therapeutics and Drug Delivery: A Multi-Disciplinary Approach*, Reddy, Ed. (CRC Press 1995); Kaur and Kanwar, Drug Dev Ind Pharm. 2002 May; 28(5): 473-93; *Clinical Ocular Pharmacology*, Bartlett et al. (Butterworth-Heinemann; 4th edition (Mar. 15, 2001)); and *Ophthalmic Drug Delivery Systems* (*Drugs and the Pharmaceutical Sciences: a Series of Textbooks and Monographs*), Mitra (Marcel Dekker; 2nd Rev&Ex edition (Mar. 1, 2003)).

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polytheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer. Such methods include those described in U.S. Pat. No. 6,468,798.

Administration of a therapeutic composition described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

Compositions comprising nucleic acid compounds can also be administered by any method suitable for administration of nucleic acid agents. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996). In some embodiments, the nucleic acid compounds comprise naked DNA, and are administered locally by injection, e.g., as described herein.

In some embodiments, the compositions are prepared with carriers that will protect the active ingredient against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially, e.g., from Alza Corporation or Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Dosage, toxicity and therapeutic efficacy of the compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

An "effective amount" is an amount sufficient to effect beneficial or desired results. For example, a therapeutic amount is one that achieves a desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions of the invention can include a single treatment or a series of treatments.

The pharmaceutical compositions can be included in a container, pack, or dispenser together with instructions for administration.

Nucleic Acids for Expression

The therapeutic compositions described herein can include nucleic acid molecules encoding a selected protein, e.g., a protein listed in one of Tables 1-6, e.g., ALK1; these are useful, e.g., where an increase in the expression and/or activity of a selected protein is desirable. Nucleic acid molecules comprising expression constructs can be used, e.g., for in vivo or in vitro expression of a selected protein. In some embodiments, expression can be restricted to a particular cell types so as to reconstitute the function of the selected protein in a cell, e.g., a cell in which that polypeptide is misexpressed, or in which expression of that polypeptide would produce a therapeutic benefit.

A nucleic acid encoding the selected protein can be inserted in an expression vector, to make an expression construct. A number of suitable vectors are known in the art, e.g., viral vectors including recombinant retroviruses, adenovirus, adeno-associated virus, and herpes simplex virus-1, adenovirus-derived vectors, or recombinant bacterial or eukaryotic plasmids. For example, the expression construct can include: a coding region; a promoter sequence, e.g., a promoter sequence that restricts expression to a selected cell type, a conditional promoter, or a strong general promoter; an enhancer sequence; untranslated regulatory sequences, e.g., a 5'untranslated region (UTR), a 3'UTR; a polyadenylation site; and/or an insulator sequence. Such sequences are known in the art, and the skilled artisan would be able to select suitable sequences. See, e.g., Current Protocols in Molecular Biology, Ausubel, F. M. et al. (eds.) Greene Publishing Associates, (1989), Sections 9.10-9.14, and other standard laboratory manuals.

Expression constructs can be administered in any biologically effective carrier, e.g. any formulation or composition capable of effectively delivering the component gene to cells in vivo. Viral vectors transfect cells directly; plasmid DNA can be delivered with the help of, for example, cationic liposomes (e.g., Lipofectin) or derivatized (e.g. antibody conjugated), polylysine conjugates, gramicidin S, artificial viral envelopes or other such intracellular carriers, as well as direct injection of the gene construct or $CaPO_4$ precipitation. In some embodiments, the nucleic acid is applied "naked" to a cell, i.e., is applied in a simple buffer without the use of any additional agents to enhance uptake. See, e.g., Current Protocols in Molecular Biology, Ausubel, F. M. et al. (eds.) Greene Publishing Associates, (1989), Sections 9.10-9.14 and other standard laboratory manuals.

In clinical settings, the nucleic acids can be introduced into a subject by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by a targeted gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054-3057).

Inhibitory Nucleic Acid Molecules

The therapeutic compositions described herein can include inhibitory nucleic acid molecules that are targeted to a selected target RNA encoding a protein listed in one of Tables 1-6, e.g., antisense, siRNA, ribozymes, and aptamers; these are useful, e.g., where a decrease in the expression and/or activity of a target protein is desirable. Based upon sequences known in the art, one of skill in the art can easily choose and synthesize any of a number of appropriate inhibitory nucleic acid molecules for use in accordance with the present invention. For example, a "gene walk" comprising a series of oligonucleotides of 15-30 nucleotides spanning the length of a target nucleic acid can be prepared, followed by testing for inhibition of target gene expression, to provide an antisense sequence. Optionally, gaps of 5-10 nucleotides can be left between the oligonucleotides to reduce the number of oligonucleotides synthesized and tested. Similar methods can be used to generate siRNAs, aptamers, and ribozymes siRNA Molecules RNAi is a process whereby double-stranded RNA (dsRNA, also referred to herein as si RNAs or ds siRNAs, for double-stranded small interfering RNAs,) induces the sequence-specific degradation of homologous mRNA in animals and plant cells (Hutvagner and Zamore, Curr. Opin. Genet. Dev.: 12, 225-232 (2002); Sharp, Genes Dev., 15:485-490 (2001)). In mammalian cells, RNAi can be triggered by 21-nucleotide (nt) duplexes of small interfering RNA (siRNA) (Chiu et al., Mol. Cell. 10:549-561 (2002); Elbashir et al., Nature 411:494-498 (2001)), or by micro-RNAs (miRNA), functional small-hairpin RNA (shRNA), or other dsRNAs which are expressed in vivo using DNA templates with RNA polymerase III promoters (Zeng et al., Mol. Cell 9:1327-1333 (2002); Paddison et al., Genes Dev. 16:948-958 (2002); Lee et al., Nature Biotechnol. 20:500-505 (2002); Paul et al., Nature Biotechnol. 20:505-508 (2002); Tuschl, T., Nature Biotechnol. 20:440-448 (2002); Yu et al., Proc. Natl. Acad. Sci. USA 99(9):6047-6052 (2002); McManus et al., RNA 8:842-850 (2002); Sui et al., Proc. Natl.

Acad. Sci. USA 99(6):5515-5520 (2002).)

The nucleic acid molecules or constructs can include dsRNA molecules comprising 16-30, e.g., 16, 17, 18, 19,20, 21, 22, 23,24, 25, 26, 27, 28,29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is complementary to the first strand. The dsRNA molecules can be chemically synthesized, or can transcribed be in vitro from a DNA template, or in vivo from, e.g., shRNA. The dsRNA molecules can be designed using any method known in the art; a number of algorithms are known, and are commercially available. Gene walk methods can be used to optimize the inhibitory activity of the siRNA.

The inhibitory nucleic acid compositions can include both siRNA and modified siRNA derivatives, e.g., siRNAs modified to alter a property such as the pharmacokinetics of the composition, for example, to increase half-life in the body, as well as engineered RNAi precursors.

siRNAs can be delivered into cells by methods known in the art, e.g., cationic liposome transfection and electroporation. siRNA duplexes can be expressed within cells from engineered RNAi precursors, e.g., recombinant DNA constructs using mammalian Pol III promoter systems (e.g., H1 or U6/snRNA promoter systems (Tuschl (2002), supra) capable of expressing functional double-stranded siRNAs; (Bagella et al., J. Cell. Physiol. 177:206-213 (1998); Lee et al. (2002), supra; Miyagishi et al. (2002), supra; Paul et al. (2002), supra; Yu et al. (2002), supra; Sui et al. (2002), supra).

Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al. (1998), 30 supra, Lee et al. (2002), supra; Miyagishi et al. (2002), supra; Paul et al. (2002), supra; Yu et al. (2002), supra; Sui et al. (2002) supra). Constructs containing siRNA sequence under the control of T7 promoter also make functional siRNAs when cotransfected into the cells with a vector expression T7 RNA polymerase (Jacque (2002), supra).

Antisense

An "antisense" nucleic acid can include a nucleotide sequence that is complementary to a "sense" nucleic acid encoding a protein, e.g., complementary to the coding strand of a double-stranded cDNA molecule or complementary to a TEF mRNA sequence. The antisense nucleic acid can be complementary to an entire coding strand of a target sequence, or to only a portion thereof. In another embodiment, the antisense nucleic acid molecule is antisense to a "noncoding region" of the coding strand of a nucleotide sequence (e.g., the 5' and 3' untranslated regions).

An antisense nucleic acid can be designed such that it is complementary to the entire coding region of a target mRNA, but can also be an oligonucleotide that is antisense to only a portion of the coding or noncoding region of the target mRNA. For example, the antisense oligonucleotide can be complementary to the region surrounding the translation start site of the target mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In some embodiments, the antisense nucleic acid molecule is an α-anomeric nucleic acid molecule. An α-anomeric nucleic acid molecule forms specific double-stranded hybrids with complementary RNA in which, contrary to the usual β-units, the strands run parallel to each other (Gaultier et al., Nucleic Acids. Res. 15:6625-6641 (1987)). The antisense nucleic acid molecule can also comprise a 2'-o-methylribonucleotide (Inoue et al. Nucleic Acids Res. 15:6131-6148 (1987)) or a chimeric RNA-DNA analogue (Inoue et al. FEBS Lett., 215:327-330 (1987)).

In some embodiments, the antisense nucleic acid is a morpholino oligonucleotide (see, e.g., Heasman, Dev. Biol. 243: 209-14 (2002); Iversen, Curr. Opin. Mol. Ther. 3:235-8 (2001); Summerton, Biochim. Biophys. Acta. 1489:141-58 (1999).

Target gene expression can be inhibited by targeting nucleotide sequences complementary to a regulatory region (e.g., promoters and/or enhancers) to form triple helical structures that prevent transcription of the Spt5 gene in target cells. See generally, Helene, Anticancer Drug Des. 6:569-84 (1991); Helene, Ann. N.Y. Acad. Sci. 660:27-36 (1992); and Maher, Bioassays 14:807-15 (1992). The potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Ribozymes

Ribozymes are a type of RNA that can be engineered to enzymatically cleave and inactivate other RNA targets in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art. A ribozyme having specificity for a target nucleic acid can include one or more sequences complementary to the nucleotide sequence of a cDNA encoding a protein described herein, and a sequence having known catalytic sequence responsible for mRNA cleavage (see U.S. Pat. No. 5,093,246 or Haselhoff and Gerlach Nature 334:585-591 (1988)). For example, a derivative of a Tetrahymena L-19 IVS RNA can be constructed in which the nucleotide sequence of the active site is complementary to the nucleotide sequence to be cleaved in a target mRNA. See, e.g., Cech et al. U.S. Pat. No. 4,987,071; and Cech et al. U.S. Pat. No. 5,116,742. Alternatively, a target mRNA can be used to select a catalytic RNA having a specific ribonuclease activity from a pool of RNA molecules. See, e.g., Bartel and Szostak, Science 261:1411-1418 (1993).

Administration of Nucleic Acid Molecules

The nucleic acid molecules described herein can be administered to a subject (e.g., by direct injection at a tissue site), or generated in situ. For example, inhibitory nucleic acid molecules can be administered such that they hybridize with or bind to cellular mRNA and/or genomic DNA encoding a target protein to thereby inhibit expression of the protein, e.g., by inhibiting transcription and/or translation. Nucleic acid molecules that encode an active agent are generally administered such that they enter a cell and are expressed therein.

In some embodiments, the nucleic acid molecules can be administered selectively, e.g., by local injection, or modified to target selected cells (e.g., by the use of a tissue-specific promoter) and then administered systemically. For systemic administration, nucleic acid molecules can be modified such that they specifically bind to receptors or antigens expressed on a selected cell surface, e.g., by linking the nucleic acid nucleic acid molecules to peptides or antibodies that bind to cell surface receptors or antigens. The nucleic acid nucleic acid molecules can also be delivered to cells using vectors known in the art, e.g., as described herein. To achieve sufficient intracellular concentrations of the inhibitory nucleic acid molecules, vector constructs in which the inhibitory nucleic acid nucleic acid molecule is placed under the control of a promoter, e.g., a strong promoter can be used. Methods for creating suitable vectors, and choosing promoters, are known in the art.

Methods of Treatment

The polypeptides and nucleic acids described herein, e.g., ALK1 polypeptides (e.g., SEQ ID NO:1) or polynucleotides (e.g., SEQ ID NO:2), and active fragments thereof, are useful in the treatment of disorders associated with neovascularization, i.e., abnormal angiogenic processes, e.g., disorders in the formation of blood vessels. Typically, the disorder will stem from overformation of blood vessels, or formation of blood vessels in an unwanted area, e.g., in the avascular regions of the eye, e.g., retinopathies, or in a tumor, e.g., a cancerous or benign tumor. For example, the ophthalmological disorder can be age-related macular degeneration, where new blood vessels grow under the retina, or diabetic retinopathy, where abnormal vessels grow on top of the retina. Other ophthalmological disorders include retinopathy of prematurity, corneal graft rejection, glaucoma, herpetic and infectious keratitis, ocular ischemia, neovascular glaucoma, corneal, uveal and iris neovascularization, orbital and eyelid tumors, Stevens Johnson Syndrome, ocular cicatricial pemphigoid, wounds, and ocular surface diseases. The disorder can be characterized by, for example, corneal, retinal, choroidal, uveal, or iris neovascularization The disorder may stem from the formation of blood vessels that deliver blood to a tissue, e.g., a primary or metastatic cancerous or benign tumors, e.g., cancer. A metastatic tumor can arise from a multitude of primary tumor types, including but not limited to those of prostate, colon, lung, breast and liver origin.

As used herein, the terms "cancer," "hyperproliferative," and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair; thus, the methods include administration of a compound identified by a method described herein to maintain avascularity during wound healing. In this embodiment, the ophthalmological disorder is a wound, including both accidental as well as intentional wounds (e.g., surgical wounds).

In some embodiments, the ophthalmological disorder is a cancer of the eye, e.g., eyelid tumors, e.g., malignant eye lid tumors, benign eye lid tumors, basal cell carcinoma, squamous cell carcinoma, sebaceous cell carcinoma, and malignant melanoma; conjunctival tumors, e.g., pigmented conjunctival tumors, melanoma and primary acquired melanosis with atypia, squamous conjunctival neoplasia, conjunctival lymphoma, and Kaposi's Sarcoma; iris tumors, e.g., iris melanoma, iris pigment epithelial cyst, anterior uveal metastasis, and pearl cyst of the iris; infiltrative intraocular tumors, e.g., multiple myeloma, lymphoma, and leukemia; choroidal tumors, e. g., choroidal melanoma, choroidal metastasis, choroidal nevus, choroidal hemangioma, choroidal osteoma, and Nevus of Ota; retinal tumors, e.g., retinoblastoma, retinal pigment epithelial tumors, retinal pigment epithelial hypertrophy, von Hippel angioma; optic nerve tumors, e.g., melanocytoma, melanoma, meningioma, circumpapillary metastasis; orbital tumors, e.g., lymphangioma, cavernous hemangioma, meningioma, mucocele, rhabdomyosarcoma, orbital pseudotumor, adenoid cystic carcinoma, periocular hemangioma of childhood; cancers of the ocular adnexa, e.g., lacrimal gland carcinomas such as adenoid cystic carcinoma and mucoepidermal epithelioma;

and metastatic ocular tumors, e.g., metastatic choroidal melanoma, and metastatic retinoblastoma.

As used in this context, to "treat" means to ameliorate at least one symptom associated with abnormal angiogenesis as well as reduce neovascularization. For the treatment of cancers and solid tumors, to "treat" includes inhibition of the growth of blood vessels resulting in a lack of nutrients for the tumors and/or cancer cells needed by the tumor for its growth. Tumors and growths will decrease in size and possibly disappear. Administration of a therapeutically effective amount of a composition for the treatment of arthritic conditions will result in decreased blood vessel formation in cartilage, specifically joints, resulting in increased mobility and flexibility in these regions. In ophthalmologic conditions, administration of a therapeutically effective amount of a composition described herein will reduce the formation of extraneous blood vessels in the retina, resulting in unobstructed or less obstructed vision. In the treatment of disorders such as cancer, administration of a therapeutically effective amount of a composition described herein will inhibit the growth and/or further formation of blood vessels, thereby inhibiting the formation of any lesions and/or tumors that arise.

Methods of Screening

The invention includes methods for screening test compounds, e.g., polypeptides, polynucleotides, inorganic or organic large or small molecule test compounds, to identify agents useful in the treatment of disorders associated with neovascularization, e.g., as described herein.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be natural products or members of a combinatorial chemistry library. A set of diverse molecules can be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of libraries, e.g., small molecule libraries, are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptides or peptidomimetic molecules. In some embodiments, the test compounds are nucleic acids, e.g., antisense, RNAi, or aptamers.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample, e.g., a cell or living tissue or organ, e.g., an eye, and one or more effects of the test compound is evaluated. In a cultured or primary cell for example, the ability of the test compound to modulate expression of one or more of the proteins listed in Tables 1-6 can be evaluated. In the eye, for example, the ability of the test compounds to modulate expression of one or more of the proteins listed in Tables 1-6 can be evaluated.

Methods for evaluating each of these effects are known in the art. For example, ability to modulate expression of a protein can be evaluated at the gene or protein level, e.g., using quantitative PCR or immunoassay methods. In some embodiments, high throughput methods, e.g., protein or gene chips as are known in the art (see, e.g., Ch. 12, Genomics, in Griffiths et al., Eds., *Modem Genetic Analysis*, 1999, W. H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect an effect on two, three, four, five or more of the proteins listed in Tables 1-6.

Compounds identified as "hits" (e.g., test compounds that demonstrate an ability to modulate, i.e., cause an increase or decrease in levels, expression, or activity, of one or more of the proteins listed in Tables 1-6) in the first screen can be selected and systematically altered, e.g., using rational design, to optimize binding affinity, avidity, specificity, or other parameter. Such optimization can also be screened for using the methods described herein. Thus, in one embodiment, the invention includes screening a first library of small molecules using a method known in the art and/or described herein, identifying one or more hits in that library, subjecting those hits to systematic structural alteration to create a second libraries of compounds structurally related to the hit, and screening the second library using the methods described herein.

Small molecules identified as hits can be considered candidate therapeutic compounds, useful in treating disorders associated with neovascularization, as described herein. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to an animal model of a disorders associated with neovascularization, as described herein. The animal can be monitored for a change in the disorder, e.g., for an improvement in a parameter of the disorder, e.g., a parameter related to clinical outcome. In some embodiments, the parameter is unwanted vascularisation, and an improvement would be a decrease in the levels of vascularisation.

One of skill in the art will appreciate that the methods described herein can be performed on non-rodent, e.g., human samples, e.g., samples obtained from human fetuses at different stages of development, as well as samples at substantially the same stage of development, but in pathological and non-pathological stages. For example, a surgical specimen from a subject with a disorder, e.g., retinopathy of prematurity or retrolental fibroplasias, can be used, and compared with a normal, unaffected control, e.g., an age-matched control.

The invention is further described in the following examples, which do not limit the scope of the invention described in the claims.

EXAMPLES

Example 1

Observation of Whole-Mount Specimens

To document the changes in the hyaloid vascular system associated with development in the cornea, whole-mount specimens were observed.

A total of 44 C57BL/6 newborn male and female litters were obtained from Jackson Laboratories (Bar Harbor, Me.) were used for the experiments described herein. The age of the newborn mice was expressed in terms of post-gestational days. The newborn mice were sacrificed on post-gestational days 1, 4, 8, 16, 24, and 30 (i.e., PI, p4, p16, p24, and P30). Four eyes per each post-gestational day were used for the histological study. For the lens and vitreous protein extraction were used 20 eyes of P 1 mice, 20 eyes of P 4 mice, 12 eyes of P 8 mice and 12 eyes of P 16 mice. Each of the 12 newborn mice used for the histological study was perfused with 4% paraformaldehyde in PBS under general anesthesia administered by intramuscular injection of a mixture of ketamine (200 mg/kg) and xylazine (10 mg/kg). The eyes were removed and immerse in buffered neutral formalin solution (100 ml 40% formalin, 900 ml distilled water, 4.0 gm monobasic sodium phosphate, 6.5 gm dibasic sodium phosphate), then they were embedded into paraffin and were cut in tissue slices of 5 micron each with a microkeratome. Each sample was stained with Hematoxylin-Eosin (H-E) staining.

By embryonic day 11 (E11) the hyaloid artery enters the optic cup and extends anteriorly, branching to form the vascular tunic of the lens (Smith, Systematic evaluation of the Mouse Eye: Anatomy, Pathology, and Biomethods. Pp 45-63. Sunders, 2002.). From E14 to birthday the blood vessels that occupied most of the vitreous cavity in earlier stages have become less prominent except around the lens and along the inner retinal surface; the PM and the TVL remain prominent (Smith, Systematic evaluation of the Mouse Eye: Anatomy, Pathology, and Biomethods. Pp 45-63. Sunders, 2002.).

PM

The PM of the newborn mice showed as a dense plexus of capillaries that began to regress on post-gestation day 4 and become vestigial on day 8. The PM disappeared completely in all eyes on day 16.

TVL

The radial branches of the TVL that lie on the lens surface are prominent until P4, particularly posterior to the lens equator. Later there is a gradual disappearance of the TVL and it is completely disappeared in about one third of eyes examined on day P24 and in all eyes on day P30.

HA and VHP

The HA arose from the optic disc as a single thick proximal trunk and entered the vitreous branching in several vessels of the VHP and running anteriorly to the posterior pole of the lens. As the whole eye developed in size and the volume of the vitreous increased, the VHP run toward the lens joining the TVL and became less prominent. Involution of HA and VHP has begun by day 1 and from day 12 to day 30 there is a gradual disappearance of those vessels.

These results concur with previous reports of HVS development and regression.

Example 2

Progressive Regression of HVS in the Mouse and Differential Protein Expression Profile This example describes the use of a proteomic approach to try to decipher the biochemical events coexisting with the progressive regression of the HVS. The proteomic analysis provided an opportunity to compare different stages of the mouse eye development, to identify specific qualitative and quantitative protein changes, associated with the early maintenance and later regression of the HVS.

Therefore to fully characterize and analyze such a dynamic process, experiments should be performed that capture the protein expression profiles of the lens and the vitreous at the various stages of blood vessel regression.

To prepare mouse lens and vitreous for 2-D electrophoresis, 32 newborn mice were decapitated. The eyes were enucleated and then frozen at −80 degrees Celsius. The frozen eyes were scraped with a blade to remove cornea, aqueous humor, conjunctiva, sclera, iris, ciliary body, uvea and retina and to obtain the lens surrounded by PM and TVL and the primary vitreous containing VHP.

The scraping was done on a dry-ice bed to prevent the specimen from warming up and the consequent protein denaturation, melting of the tissue and contamination of the specimen by eye components different from lens and primary vitreous.

Twenty specimens of P1, 20 specimens of P4, 12 specimens of P8, and 12 specimens of P16 were independently solubilized in 250 µl of Total Protein Extraction Buffer (7 M urea, 2 M thiourea, 1% (w/v) ASB-14 detergent, 40 mM Tris base, 0.001% bromophenol blue, 20% carrier ampholyte; Biorad Laboratories, Hercules, CA) plus 2 µl of 200 mM tributylphosphine by mechanically homogenizing them with an electrical tissue homogenizer for 5 minutes, in an ice-water bath to prevent the specimens from warming up.

The homogenate was transferred into 1.5 ml micro centrifuge tubes and the protein extracts were cleared by centrifugation at 14,000 rpm for 20 minutes at 4° Celsius to remove particulates. The protein concentration of the cleared supernatants was determined by using a compatible protein assay (Biorad Laboratories, Hercules, Calif.), and samples were stored at −80° Celsius until use.

Three separate experiments were performed.

I. Differential Protein Expression in P1, P4, P8, P16 Using IPG Strips pH 3-10

A time course experiment was designed to examine the changes in protein expression at the critical time points throughout the HVS regression process.

Lens and vitreous of P1, P4, P8 and P16 were selected to perform the experiment because the histological analysis showed that in post-gestation day 1 the hyaloid network is still prominent and by post-gestational day 16 the hyaloid network is already vestigial. In this experiment, three samples per each post-gestational day were loaded onto nonlinear immobilized pH gradient (IPG) gel strips (7 cm, pH 3-10) and rehydrated overnight with Rehydration/Sample Buffer (Biorad Laboratories, Hercules, Calif.).

As this is the first reported application of proteome analysis on HVS regression, several of the conditions for tissue selection and preparation were developed and optimized to obtain clean specimen of lens and vitreous to avoid the presence of proteins coming from other part of the eye on the final 2-DE gels.

Images of the 2-DE gels were captured with Molecular Imager FX Pro Plus multi-imager system and protein expression profile at each time point was compared in triplicate using the Phoretix 2D imaging analysis software.

Protein spots that were reproducibly differentially expressed in P1 and P 16 were considered for protein identification. The statistical significance of changes was evaluated using the Phoretix 2D software.

Gel bands were excised and minced into approximate 1 $mm^3$ pieces with a sterile razor blade of the Xcise technology platform from Proteome system and placed into a sterile microcentrifuge. Gel pieces were destained 3 times by adding 200 uL of 25 mM $NH_4HCO_3$ in 50% acetonitrile, dried using a SpeedVac® concentrator, alkylated and digested with trypsin (Promega, Madison, Wis., USA) in 50 mM of ammonium bicarbonate overnight to release tryptic peptides. Samples were dried in a SpeedVac® to remove residual ammonium bicarbonate. Peptides were resuspended in 50% acetonitrile with 1% formic acid solution. About 30% of the digest was subjected to nano-LC ESI IT MS/MS analysis.

A Surveyor LC pump (ThermoElectron, CA) with a C18 trapping column (300 um i.d.×1 mm, Dionex, CA) and a self-packed reversed-phase column 75 mm i.d.×15 cm (Magic C18AQ, 3 um) was used for nano-LC experiments. An LCQ Deca XP Plus ESI mass spectrometer (Thermo Electron, CA) was used for all the experiments. In data-dependent MS/MS scanning, a full MS scan between 400 and 2000 m/z was followed by five full MS/MS scans for the five most intense ions from the MS scan in all ESI. MS/MS data-dependent acquisition, followed by database searching with SEQUEST (BioWorks 3.1, ThermoElectron) allowed protein identification.

Fully tryptic peptides were matched with SEQUEST at a delta correlation ($\Delta$Cn) of greater than 0.08 and correlation (Xcorr) greater than 1.9, 2.2 and 3.5 for charged states of +1, +2 and +3, respectively. The search was performed against the whole NCBInr mouse protein sequence database, and human homologs (e.g., proteins with at least 75% identity to the mouse sequence) were identified (www.ncbi.nml.nih.gov).

Protein expression maps were generated in triplicate per each time point obtaining a reproducible separation of the protein spots on the 2-DE gels. On average, up to 1300 proteins spots could be detected in each gel with the Phoretix 2D imaging analysis software. This software provides the ability to "warp" different gel images using mathematical algorithms, improving the quality of the protein spot matching between the gels and allowing easy detection of the differences among the gels.

The 2-DE gels demonstrated a progressive lessening in the number and in the intensity of the protein spots from P1 to P16, particularly of the proteins that migrated in the area corresponding to pI 4 to pI 7 and $M_r$ 30 kDa to 90 kDa. However, the warping of P1, P4 and P8 with P16 revealed the presence of 20 protein spots in P16 that are not present in the other gels.

This evidence suggest the presence in the earlier post-gestation days of an active protein expression coexisting with the presence of a prominent HVS and the presence in P16 of factors whose synthesis or degradation is related to the regression of the HVS itself.

For this initial study, 11 protein spots were identified, using the Phoretix 2D imaging analysis software, that were present in P1 at greater than two-fold higher levels of expression relative to P16 were selected and excised for identification. From these 11 spots, 23 differentially expressed proteins were identified (Table 1); one of them is an unnamed protein product and two of them (the serotransferrin precursor and similar to ethanol induced 6) were identified in multiple spots, as they are post-translationally modified versions of the same protein.

TABLE 1

Proteins Present in P1 at >2X levels of expression in P16

| # | PROTEIN | MOUSE GENE BANK # | HUMAN HOMOLOG GENE BANK # |
|---|---|---|---|
| 1. | alpha fetoprotein | 31982513 | 120042 |
| 2. | Calmodulin | 115512 | 56404656 |
| 3. | protein product 19263784 | 19263784 | (—) |
| 4. | Creatine kinase | 15929689 | 34335231 |
| 5. | dermatan-4-sulfotransferase-1 | 31980715 | 18497304 |
| 6. | Ethanol induced 6 homolog | 38082607 | (—) |
| 7. | GRP1 (general receptor for phosphoinositides 1) | 31980946 | 32171221 |
| 8. | heterogeneous nuclear ribonucleoprotein K homolog | 38074994 | 51464712 |
| 9. | histidine triad nucleotide binding protein | 33468857 | 21359982 |
| 10. | immunoglobulin 9E10 heavy chain | 2505942 | (—) |
| 11. | KH-type splicing regulatory protein | 38082738 | 4808586 |
| 12. | Profilin 1 | 12846944 | 4826898 |
| 13. | prolyl 4-hydroxylase, beta polypeptide | 20913929 | 20070125 |
| 14. | protein 40 kD homolog | 38079048 | 51460993 |
| 15. | protein product 33115175 | 33115175 | (—) |
| 16. | protein product 12845853 | 12845853 | (—) |
| 17. | RAD23a homolog | 38089412 | (—) |
| 18. | Ribosomal protein S12 | 17390846 | (—) |
| 19. | ring finger and WD repeat domain 1 | 24418905 | 50233824 |
| 20. | Serotransferrin precursor | 21363012 | 136191 |
| 21. | Synovial sarcoma, X breakpoint 2 interacting protein | 21594537 | 41281571 |
| 22. | Trk-fused gene | 19353070 | 21361320 |
| 23. | Tumor rejection antigen gp96 | 15030324 | 4507677 |

All 20 of the spots differentially expressed in P16, i.e., present in P16 at greater than two-fold higher levels of expression relative to P1 were excised and identified. From these 20 spots, 39 differentially expressed proteins were identified (Table 2); four of them are unnamed protein products and eight of them (Crybb1 protein, fatty acid binding protein 5, crystallin α1, crystallin βA1, crystallin βA4, crystallin βB3, crystalline γb, and crystalline γd) were identified in different spots, as they represented modified versions or fragments of the same protein.

TABLE 2

Proteins Present in P16 at >2X levels of expression in P1

| # | PROTEIN | MOUSE GENE BANK # | HUMAN HOMOLOG GENE BANK # |
|---|---|---|---|
| 1. | protein product 38089687 | 38089687 | (—) |
| 2. | Acvrl1 protein (ALK1) | 15929282 | 4557243 |
| 3. | Albumin 1 | 19353306 | 8392890 |

TABLE 2-continued

Proteins Present in P16 at >2X levels of expression in P1

| # | PROTEIN | MOUSE GENE BANK # | HUMAN HOMOLOG GENE BANK # |
|---|---|---|---|
| 4. | Alpha enolase | 13637776 | 4433141 |
| 5. | Cathepsin 3 precursor | 19424144 | (—) |
| 6. | Cofilin 1 | 37194891 | 5031635 |
| 7. | Crybb1 protein | 22137737 | 47678381 |
| 8. | Crystallin, alpha A | 30794510 | (—) |
| 9. | Crystallin, beta A1 | 20304089 | 12056461 |
| 10. | Crystallin, beta A2 | 31088965 | 13623372 |
| 11. | Crystallin, beta A4 | 33989574 | 4503059 |
| 12. | Crystallin, beta B2 | 6681035 | 4503063 |
| 13. | Crystallin, beta B3 | 37589234 | 4758074 |
| 14. | Crystallin, gamma B | 38049551 | 4885157 |
| 15. | Crystallin, gamma C | 33990600 | 10518338 |
| 16. | Crystallin, gamma D | 34784220 | 13377002 |
| 17. | Crystallin, gamma F | 33991687 | (—) |
| 18. | Cytochrome P450 2D9 homolog | 38077646 | (—) |
| 19. | Enolase 3 | 15488630 | 16554592 |
| 20. | Fatty acid binding protein 5 | 6754450 | 30583736 |
| 21. | FX3B_MOUSE F-box/LRR-repeat protein 3B | 37537783 | (—) |
| 22. | Glyceraldehyde-3-phosphate dehydrogenase | 6679939 | 19924131 |
| 23. | Guanine nucleotide-binding protein | 15341782 | 20357526 |
| 24. | Heat shock 70 kD protein 5 | 29748016 | 24234686 |
| 25. | Heat shock cognate 71 kDa protein | 123651 | 123648 |
| 26. | Hspb1 protein | 17390597 | 4504517 |
| 27. | IgM heavy chain | 1763745 | 54780866 |
| 28. | keratin 5b homolog | 38077186 | (—) |
| 29. | keratin complex 2, basic, gene 5 | 20911031 | (—) |
| 30. | Kns17 protein | 38173736 | 9910266 |
| 31. | protein product mKIAA0585 protein | 28972291 | (—) |
| 32. | protein product mKIAA0650 protein | 37360026 | (—) |
| 33. | protein kinase, cAMP dependent regulatory | 31543509 | 38257138 |
| 34. | protein product 1333921 | 1333921 | (—) |
| 35. | protein product 26335149 | 26335149 | (—) |
| 36. | RAD50 homolog | 6679609 | 19924130 |
| 37. | Solute carrier family 20 | 28204938 | 58761541 |
| 38. | Tubulin | 33416314 | 34784746 |
| 39. | Vimentin | 31982755 | 57471648 |

II. Differential Protein Expression in P4 and P16 Using IPG Strips pH 4-7, 5-8, 7-10

The use of broad range strips allows the display of the most proteins in a single gel. With narrow-range and micro-range overlapping gradient strips, resolution is increased by expanding a small pH range across the entire width of a gel and more spots can be displayed per each sample. This is due to the extra resolving power from use of a narrower pI range per gel. Because proteins outside of the pH range of the strip are excluded, more total protein mass can be loaded per strip, allowing more proteins to be detectable.

In this experiment, three samples for P4 and three samples for P16 were loaded onto nonlinear immobilized pH gradient (IPG) 7 cm gel strips with pH 4-7, pH 5-8, pH 7-10 and rehydrated overnight with Rehydration/Sample Buffer. Isoelectric focusing (IEF) was performed with a programmed voltage gradient at 8,000 V for 5 hours.

IPG strips were prepared for the second dimension by two sequential 10 minute incubations in 6 M urea, 50 mM Tris (pH 8.8), 30% glycerol, 2% SDS, and 0.001% bromophenol blue, containing, alternately, 2% DTT or 2.5% iodoacetamide.

Following equilibration, second-dimension separation was then performed on 4-20% SDS-PAGE gels (Biorad Laboratories, Hercules Calif.) with the first-dimension IPG strip embedded in 0.5% agarose at the top. Proteins on gel were fixed in 10% acetic acid and 20% methanol for 1 hour and were then stained using SYPRO Rubin Protein Gel stain (Biorad Laboratories, Hercules Calif.). In total, 12 gels with samples were prepared and subjected to analysis for the first experiment and 6 for the second experiment.

Using the Phoretix 2D imaging analysis software, the gels were warped the P4 map was matched with the P16 map to compare and identify proteins that were differentially expression in these gels. Of the proteins with differential expression, a number of spots were selected.

Comparing P4 map pH 4-7 with P16 map pH 4-7, fifteen spots were selected that included proteins that were differentially expressed found to be clearly present in P4 and barely detectable or not detectable in P16, and another fifteen spots that were clearly present in P16 and barely detectable or not detectable in P1.

Comparing P4 map pH 5-8 with P16 map pH 5-8, three spots were found to be clearly present in P4 and barely detectable or not detectable in P16, and another seven spots were clearly present in P16 and not in P4.

Comparing P4 map pH 7-10 with P16 map pH 7-10, two spots were found to be clearly present in P4 and barely detectable or not detectable in P16, and another two spots were clearly present in P16 and barely detectable or not detectable in P4.

These 44 spots were identified using mass spectrometry analysis. The results are shown in Tables 3-4. Table 3 lists proteins that were identified as particularly interesting targets, due to their known function.

TABLE 3

Potentially Relevant Proteins

| # | PROTEIN | MOUSE GENE BANK #GI | HUMAN HOMOLOG GENE BANK #GI |
|---|---|---|---|
| 1. | protein BC031593 protein | 17512384 | (—) |
| 2. | protein Ppp3cc | 12853166 | 13937367 |
| 3. | 14-3-3 PROTEIN TAU homolog (14-3-3 PROTEIN THETA) | 12849349 | (—) |
| 4. | 143B_MOUSE 14-3-3 protein beta/alpha | 3065924 | (—) |
| 5. | 143G_HUMAN 14-3-3 protein gamma | 3065928 | (—) |
| 6. | acid phosphatase 2, lysosomal | 29150253 | 4557010 |
| 7. | Acvr1 protein | 15929282 | 4557243 |
| 8. | annexin A5; annexin V | 6753060 | 4502107 |
| 9. | Ca < 2+ > dependent activator protein for secretion | 6753238 | 34452715 |
| 10. | calcium binding protein | 2639022 | 7656952 |
| 11. | Calnexin | 56206506 | 10716563 |
| 12. | cathepsin 3 precursor | 19424144 | (—) |
| 13. | Cathepsin D | 26101892 | 4503143 |
| 14. | protein AY100450; WFIKKN-like; growth and differentiation factor | 32451494 | (—) |
| 15. | Cofilin 1 | 37194891 | 5031635 |
| 16. | Creatine kinase, brain | 10946574 | (—) |
| 17. | Cttn protein | 15030315 | 21707902 |
| 18. | development- and differentiation-enhancing factor 2; PYK2 C homolog | 51827426 | (—) |
| 19. | DiGeorge syndrome critical region gene 6 product homolog | 29144908 | (—) |
| 20. | drebrin 1; drebrin E2; drebrin A | 34328251 | 18426915 |
| 21. | fatty acid binding protein 5, epidermal | 6754450 | 4503491 |
| 22. | Fbxo9 protein | 18044861 | 53692184 |
| 23. | fibroblast growth factor 22 | 12843402 | 120050 |
| 24. | FK10_MOUSE FK506 binding protein 10 precursor | 26105984 | 7706131 |

TABLE 3-continued

Potentially Relevant Proteins

| # | PROTEIN | MOUSE GENE BANK #GI | HUMAN HOMOLOG GENE BANK #GI |
|---|---|---|---|
| 25. | golgi associated, gamma adaptin ear containing, ARF binding protein 1 | 22122347 | 48527954 |
| 26. | GRP1 (general receptor for phosphoinositides 1)-associated scaffold protein | 26094386 | 32171221 |
| 27. | H2-T10 protein | 18257363 | (—) |
| 28. | Hepatoma-derived growth factor | 34787412 | 55960780 |
| 29. | Inner centromere protein | 26353663 | 51471706 |
| 30. | integrin beta 2; integrin beta 2 (Cd18); Mac-1 beta; macrophage antigen | 26353439 | 4557886 |
| 31. | Male-specific lethal-3 homolog 1 | 11545735 | 5052315 |
| 32. | Map3k4 protein | 37590139 | 57338496 |
| 33. | Myristoylated alanine rich protein kinase C substrate | 6678768 | 57870608 |
| 34. | NRCA_MOUSE Neuronal cell adhesion molecule precursor (Nr-CAM) (NgCAM-related) | 26333200 | (—) |
| 35. | PDZ domain containing homolog | 26325701 | 58533161 |
| 36. | phosducin homolog | 7684610 | 9943842 |
| 37. | Profilin 1 | 12846944 | 4826898 |
| 38. | protein 1200008A14 | 12835962 | (—) |
| 39. | protein 2310057D15Rik | 12845067 | (—) |
| 40. | protein 2610111M03Rik | 12848227 | (—) |
| 41. | protein 2700081O15Rik | 26083118 | (—) |
| 42. | protein A830054M12 | 26090077 | (—) |
| 43. | protein AI507495 | 47523976 | (—) |
| 44. | protein AI663987 | 51708226 | (—) |
| 45. | protein AU042671 | 18044599 | (—) |
| 46. | protein BC037006 protein | 17160955 | (—) |
| 47. | protein kinase, cAMP dependent regulatory, type I beta | 15030299 | 1346362 |
| 48. | protein mKIAA0585 protein | 28972291 | (—) |
| 49. | protein mKIAA0650 | 12855134 | (—) |
| 50. | protein mKIAA1565 | 26349512 | (—) |
| 51. | protein NUF2R | 12963617 | 12667401 |
| 52. | protein phosphatase 1, regulatory (inhibitor) subunit 2 homolog | 12832826 | (—) |
| 53. | Protein phosphatase 2, regulatory subunit B (B56), beta isoform | 37718993 | 5453952 |
| 54. | protein Prkcsh | 14602601 | 15488917 |
| 55. | protein putative 40-2-3 protein | 26346029 | 15216162 |
| 56. | protein Rbbp6 protein | 30851332 | 49522749 |
| 57. | protein tyrosine phosphatase, receptor type, S | 25092609 | 2842713 |
| 58. | Ras-GTPase-activating protein SH3-domain binding protein | 56800092 | 54695638 |
| 59. | SH3-domain GRB2 homolog | 31560792 | 55661111 |
| 60. | S-phase kinase-associated protein 1A | 31560543 | (—) |
| 61. | Tnf receptor-associated factor 3 | 6755865 | 22027620 |
| 62. | Tnks protein | 34980999 | (—) |
| 63. | Tripartite motif protein 28 | 59807693 | 3183179 |
| 64. | Trk-fused gene | 19353070 | 21361320 |
| 65. | Ubiquilin 2 | 34328236 | 17426453 |
| 66. | ubiquitin-like 1 (sentrin) activating enzyme E1B; anthracycline-associated | 7709986 | (—) |
| 67. | Valosin containing protein | 30023842 | 55662798 |
| 68. | zinc finger protein 120 isoform 2 | 31044493 | (—) |
| 69. | zinc finger protein 462; gene trap insertion site 4-2 | 26327260 | 8036504 |
| 70. | Zyx protein | 32451799 | 33870614 |
| 71. | GRP1 (general receptor for phosphoinositides 1)-associated scaffold | 28277382 | |
| 72. | otoferlin [Mus musculus] | 51831108 | |
| 73. | Cofilin 1, non-muscle [Mus musculus] | 28374265 | |
| 74. | cathepsin 3 precursor [Mus musculus] | 31560606 | |
| 75. | Heat shock 70 kD protein 5 (glucose-regulated protein) [Mus musculus] | 31981721 | |
| 76. | Acvrl1 protein [Mus musculus] | 6752957 | |
| 77. | Tnf receptor-associated factor 3 [Mus musculus] | 6755864 | |
| 78. | integrin alpha 2; integrin alpha 2 (Cd49b); VLA-2 receptor, alpha 2 | 41054730 | |
| 79. | H2-T10 protein [Mus musculus] | 51770266 | |
| 80. | fibrillin-1 precursor - mouse | 6755774 | |
| 81. | protein tyrosine phosphatase, receptor type, S [Mus musculus] | 33286922 | |
| 82. | transient receptor potential cation channel, subfamily M, member 3 | 59889895 | |
| 83. | calcium channel, voltage-dependent, L type, alpha 1S subunit | 51712446 | |
| 84. | Krt1-15 protein | 6680601 | |
| 85. | stress-induced phosphoprotein 1; stress-inducible protein; IEF SSP 352 | 14389430 | |
| 86. | Hepatoma-derived growth factor | 31560690 | |
| 87. | Lmnb1 protein | 6754555 | |
| 88. | Myristoylated alanine rich protein kinase C substrate | 6678767 | |
| 89. | phosphoglycerate kinase | 30802044 | |
| 90. | acetyl-Coenzyme A acetyltransferase 1 | 31542049 | |

Table 4 is a list of those proteins with unknown function that are differentially expressed during development of the HVS.

TABLE 4

Differentially Expressed Unknown Proteins

| # | PROTEIN | MOUSE GENE BANK #GI | SIGNIFICANT HOMOLOGY with | Possible function (by homology) |
|---|---|---|---|---|
| 1. | protein 4930477M19 | 29244200 | solute carrier family 22 | |
| 2. | protein XP_358378 | 38089454 | LOC348180 protein | |
| 3. | protein XP_148779 | 38082098 | unknown | |
| 4. | protein 4732456N10 | 29244176 | keratin 5 | |
| 5. | protein D630003M21 | 29244074 | KIAA1755 protein homolog | |

TABLE 4-continued

Differentially Expressed Unknown Proteins

| # | PROTEIN | MOUSE GENE BANK #GI | SIGNIFICANT HOMOLOGY with | Possible function (by homology) |
|---|---|---|---|---|
| 6. | protein MGC11770 | 21450213 | alanyl-tRNA synthetase homolog | |
| 7. | protein 4832416E03 | 27370264 | alanyl-tRNA synthetase homolog | |
| 8. | protein S25715 protein - mouse | 284778 | unknown | |
| 9. | protein 4932412H11 | 27370338 | leucine-rich repeat containing protein homolog | |
| 10. | protein product 26390223 | 26390223 | protein disulfide isomerase homolog | |
| 11. | protein product 26351281 | 26351281 | Titin homolog | |
| 12. | protein product 1333921 | 1333921 | crystallin, gamma A | |
| 13. | protein product 26354026 | 26354026 | tropomyosin 3 | |
| 14. | protein product 26338367 | 26338367 | unknown | |
| 15. | protein product 26329025 | 26329025 | unknown | |
| 16. | protein product 12852979 | 12852979 | PDZ domain containing 1 | |
| 17. | protein product 26325560 | 26325560 | unknown | |
| 18. | protein product 26354901 | 26354901 | ankyrin homolog | |
| 19. | protein product 26340818 | 26340818 | unknown | |
| 20. | protein product 26346649 | 26346649 | tropomyosin 1 | |
| 21. | protein product 26346108 | 26346108 | Interferon-induced protein | |
| 22. | protein product 26335149 | 26335149 | endothelial progenitor cells, angiopoietin homolog | |
| 23. | protein product 38257031 | 38257031 | oogenesin 1 | |
| 24. | protein product 26342222 | 26342222 | High mobility group homolog | |
| 25. | protein product 26351025 | 26351025 | unknown | |
| 26. | protein for MGC: 70225 | 38328278 | heterogeneous nuclear ribonucleoprotein A3 | |
| 27. | protein for MGC: 69648 | 38328232 | unknown | |
| 28. | protein for MGC: 65613 | 32451767 | Snx25 protein | |
| 29. | protein for MGC: 70304 | 38328220 | septin 11 | |
| 30. | protein for MGC: 66590 | 38348540 | unknown | |
| 31. | protein for MGC: 74310 | 38174349 | T-complex protein 10c | |
| 32. | protein for MGC: 66854 | 38173718 | nestin homolog | |
| 33. | cDNA 4930513F16 | 29789229 | IQ calmodulin-binding motif containing protein | |
| 34. | cDNA 1110021E09 | 30354152 | unknown | |
| 35. | cDNA 4930578C19 | 30424860 | nucleotide triphosphate hydrolases | apoptosis |
| 36. | cDNA 6030404K05 gene | 30425216 | C2H2 zinc-finger at its N-terminal region | |
| 37. | cDNA C730025I08 gene | 30425272 | RETINOL DEHYDROGENASE | |
| 38. | cDNA 2610019P18 | 30519939 | unknown | |
| 39. | cDNA C730027J19 gene | 30520215 | rat hypertension-associated homolog | |
| 40. | cDNA 2610036L13 | 31127295 | cell division cycle associated 5 | angiogenesis |

TABLE 4-continued

Differentially Expressed Unknown Proteins

| # PROTEIN | MOUSE GENE BANK #GI | SIGNIFICANT HOMOLOGY with | Possible function (by homology) |
|---|---|---|---|
| 41. cDNA 5730444A13 | 31542010 | G-protein beta WD-40 repeats | apoptosis |
| 42. cDNA 5230400J09 | 33859785 | duf containing peotein, zeta-crystallin | |
| 43. cDNA 1500011H22 | 34784371 | unknown | |
| 44. cDNA 9030623C06 | 34980904 | keratin 21, type I, cytoskeletal | |
| 45. cDNA 6430598A04 gene | 34980939 | netrin-G1 ligand NGL-1 | apoptosis |
| 46. cDNA 1500031K13 | 37589970 | calcium binding protein 39-like | |
| 47. cDNA 3110001E11 | 38075065 | unknown | |
| 48. cDNA 1700020H17 | 38075351 | molybdopterin synthase sulfurylase | |
| 49. cDNA 4933432B09 | 38077919 | unknown | |
| 50. cDNA 1110037F02 | 38078070 | unknown | |
| 51. cDNA 5730537H01 | 38084391 | mRNA-decapping enzyme (DCP2) | |
| 52. cDNA E330005F07 gene | 38089151 | microtubule binding protein hook3, GTPase | |
| 53. cDNA B630009I04 | 38090459 | activating signal cointegrator 1 complex | |
| 54. cDNA 9130006A14 | 38091346 | *Mus musculus* RasGEF domain family, Cell Division Control Protein 25 | proliferation and apoptosis |
| 55. cDNA F830010I22 | 38091563 | TENSIN homolog | |
| 56. cDNA A930040G15 | 46048307 | unknown | |
| 57. cDNA 4432411E13 | 51769098 | hyperplastic discs protein, tumor suppressor | |
| 58. cDNA C130068M19 | 59858553 | beta WD-40 repeats containing protein | |

Differential Protein Expression in P1, P4, P8, P16 Using IPG Strips pH 3-10 and Phosphostaining In this experiment, two samples per each post-gestational day were loaded onto nonlinear immobilized pH gradient (IPG) gel strips (7 cm, pH 3-10) and rehydrated overnight with Rehydration/Sample Buffer (Biorad Laboratories, Hercules, Calif.). The same steps were followed for the gel electrophoresis, and then proteins on gel were fixed in 10% acetic acid and 20% methanol overnight. Each of the 8 gels was incubated three times for 10 minutes with 100 mL of $dH_2O$ with gentle agitation in order to remove all of the methanol and acetic acid from the gel.

Then each gel was incubated in the dark in 50 mL of Pro-Q® Diamond phosphoprotein gel stain with gentle agitation for 75-120 minutes (Molecular Probes Laboratories); each gel was destained for two times in 80-100 mL of Destain Solution (Molecular Probes Laboratories) at room temperature, protected from light. Images of each gel were taken with the Image acquisition system Molecular Imager FX Pro Plus. Every gel was then stained for three hours with SYPRO Rubin Protein gel Stain (Biorad Laboratories, Hercules Calif.), and proteins on the gel were fixed twice in 10% acetic acid and 20% methanol for 1 hour. Images of each gel were taken with the Image acquisition system Molecular Imager FX Pro Plus.

The proprietary fluorescent stain of Pro-Q® Diamond phosphoprotein gel staining (Molecular Probes Laboratories) allows direct in-gel detection of phosphate groups attached to tyrosine, serine or threonine residues. The comparison between the images obtained from P1 and P16 gels stained with the phosphostain showed a different pattern of protein activation. Thirteen protein spot were identified with mass spectroscopy that were present in P1 but not in P16, and nine protein spots present in P16 but not in P1. Proteins identified by this method are listed in Table 5.

TABLE 5

PROTEINS WITH ALTERATIONS IN PHOSPHORYLATION

| PROTEIN | HUMAN GI # | MOUSE GI# |
|---|---|---|
| 1810015P09Rik protein | | 21411262 |
| 2610111M03Rik protein | | 19353142 |
| a disintegrin and metalloprotease domain 4; a disintegrin and metallop | | 27923590 |
| Albumin 1 | | 19353306 |
| alpha fetoprotein; alpha-foetoprotein | | 31982513 |
| antibody heavy chain variable region | | 1518293 |
| B230317C12Rik protein | | 37994630 |
| $Ca^{2+}$ dependent activator protein for secretion | | 6753238 |
| Calnexin | | 25955477 |
| CRAA_MOUSE Alpha crystallin A chain, major component | | 117369 |
| Cryab protein | | 14789702 |
| Crybb1 protein | | 22137737 |
| crystallin, alpha A; lens opacity 18; crystallin, alpha 1; alpha-A-cry | | 30794510 |
| crystallin, beta A1 | | 20304089 |

TABLE 5-continued

PROTEINS WITH ALTERATIONS IN PHOSPHORYLATION

| PROTEIN | HUMAN GI # | MOUSE GI# |
|---|---|---|
| Crystallin, beta A2 | | 31088965 |
| Crystallin, beta B3 | | 37589234 |
| crystallin, gamma B | | 38049551 |
| Crystallin, gamma C | | 33990600 |
| Crystallin, gamma D | | 34784220 |
| Crystallin, gamma F | | 33991687 |
| Crystallin, gamma S | 46854370 or 47124529 | 33989585 |
| drebrin 1; drebrin E2; drebrin A | | 34328251 |
| dynein, axonemal, heavy polypeptide 9 | | 38091406 |
| Facl6 protein | | 16359313 |
| gamma 4-crystallin | | 51017 |
| Heat shock 70 kD protein 5 (glucose-regulated protein) | | 29748016 |
| Heat shock protein 1, alpha | | 28436908 |
| heat shock protein 1, beta; heat shock protein, 84 kDa 1; heat shock 90 | | 6680305 |
| heat shock protein, 110 kDa | | 13278232 |
| Hook homolog 1 | | 38197327 |
| HS7C_MOUSE Heat shock cognate 71 kDa protein | | 123651 |
| Hspcb protein | | 29612561 |
| hypothetical protein 4732456N10 | | 29244176 |
| IgM heavy chain | | 1763745 |
| integrin alpha 2; integrin alpha 2 (Cd49b); VLA-2 receptor, alpha 2 sub | | 6680478 |
| laminin, beta 2; Laminin S | | 31982223 |
| laminin, gamma 2; nicein, 100 kD; nicein, 100 kDa | | 19115956 |
| Lmnb1 protein | | 34849832 |
| mannosidase 2, alpha 2; alpha mannosidase IIx; mannosidase, alpha, cla | 51477716 | 27777691 |
| mKIAA0723 protein | | 37360062 |
| mutS homolog 5 | | 7305281 |
| Myristoylated alanine rich protein kinase C substrate | | 28302374 |
| Nasp protein | | 13435642 |
| nuclear autoantigenic sperm protein | | 13384598 |
| Pleckstrin homology-like domain, family A, member 2 | | 17512344 |
| prolactin-like protein E; prolactin-like protein G | | 6679471 |
| protein tyrosine phosphatase, receptor type, S | | 25092609 |
| PSD3_MOUSE 26S proteasome non-ATPase regulatory subunit 3 (26S proteasome reg | | 19856169 |
| Rbbp6 protein | | 30851332 |
| Ribosomal protein S27a | | 12805285 |
| RIKEN cDNA 0610041L09 | | 21313618 |
| RIKEN cDNA 1500011H22 | | 34784371 |
| RIKEN cDNA 1700028P14 | | 29436989 |
| RIKEN cDNA 3000003F02 | | 27369583 |
| RIKEN cDNA 4432411E13 | | 38077035 |
| RIKEN cDNA 6030404K05 gene | | 30425216 |
| RIKEN cDNA A030005L19 | | 13386450 |
| RIKEN cDNA D430026P16 gene | | 28893017 |
| RIKEN cDNA F830010I22 gene | | 38091563 |
| S25715 hypothetical protein - mouse (fragment) | | 284778 |
| Serine (or cysteine) proteinase inhibitor, clade A, member 1b [Mus muscu | | 19343549 |
| Serine (or cysteine) proteinase inhibitor, clade A, member 1e [Mus muscu | | 38174657 |
| Serpina 1b protein | | 15277553 |
| similar to 60S ribosomal protein L10 (QM protein homolog) [Mus musculu | | 38079574 |
| similar to alpha-2-HS-glycoprotein homolog - mouse | | 38080571 |
| similar to alpha-tubulin | | 38050521 |
| similar to ATP-binding cassette, sub-family A, member 12 isoform b [Mu | | 38049559 |
| similar to Crybb1 protein | | 38074960 |
| similar to Elongation factor 1-alpha 1 (EF-1-alpha-1) (Elongation fact | | 38090266 |
| similar to heat shock protein hsp90 beta | | 38096689 |
| similar to hypothetical protein FLJ21665 | | 38074149 |
| similar to K-ALPHA-1 protein | | 38084290 |
| Similar to neuronal protein | | 28175466 |
| similar to tubulin Mbeta 1 | | 38075765 |
| similar to tubulin, beta 3 | | 38085389 |
| Solute carrier family 3, member 1 | 18490867 | 15488595 |
| S-phase kinase-associated protein 1A | | 12805297 |
| Synovial sarcoma, X breakpoint 2 interacting protein | | 21594537 |
| Tnks protein | | 34980999 |
| Tripartite motif protein 28 | | 37231553 |
| trypsinogen 10 | | 2358087 |
| trypsinogen 16 | | 16716569 |
| Tubulin, alpha 2 | | 12805487 |
| Tubulin, alpha 6 | | 20071240 |
| tubulin, beta | | 21746161 |
| Tubulin, beta 2 | | 33416314 |
| Tubulin, beta 3 | | 21595026 |
| Tubulin, beta 4 | | 32766247 |
| Tubulin, beta 5 | | 13277909 |
| ubiquitin specific protease 9, Y chromosome | | 22507351 |
| ubiquitin-like 1 (sentrin) activating enzyme E1B; anthracycline-associa | | 7709986 |
| Unknown (protein for MGC: 69991) | | 38328337 |
| unnamed protein product | | 1333921 |
| Valosin containing protein | | 29144989 |
| vimentin | 57471648 | 31982755 |
| ZIN_MOUSE Striatin 4 (Zinedin) | | 17367523 |
| 1012270B antibody L-V, anti-arsonate | | GI: 224215 |
| 2700081O15Rik protein | | 37589581 |
| 5730509E04Rik protein | | 20071529 |
| Actin-like 6 | | 29436558 |
| arylalkylamine N-acetyltransferase | | 6752938 |
| ATPase, H+ transporting, V1 subunit A, isoform 1; ATPase, H+ transport | | 31560731 |
| beaded filament structural protein 2, phakinin | | 38090061 |
| Cathepsin D | | 21450788 |
| CRAA_MOUSE Alpha crystallin A chain, major component | | 117369 |
| Creatine kinase, brain | | 15929689 |
| Cryab protein | | 14789702 |
| Crybb1 protein | | 22137737 |
| crystallin, alpha A; lens opacity 18; crystallin, alpha 1; alpha-A-cry | | 30794510 |
| crystallin, beta A1 | | 20304089 |
| Crystallin, beta A2 | | 31088965 |
| Crystallin, beta A4 | | 33989574 |
| crystallin, beta B2; betaB2-crystallin; Philly cataract | | 6681035 |
| Crystallin, beta B3 | | 37589234 |
| crystallin, gamma B | | 38049551 |
| Crystallin, gamma C | | 33990600 |
| Crystallin, gamma D | | 34784220 |
| Crystallin, gamma F | | 33991687 |
| crystallin, gamma N | | 23346485 |
| Crystallin, gamma S | | 33989585 |
| eukaryotic translation initiation factor 3, subunit 5 (epsilon) [Mus m | | 21313620 |
| G protein-coupled receptor 106; G protein coupled receptor affecting t | | 15546059 |
| gamma 4-crystallin | | 51017 |
| Hnrpk protein | | 13879427 |
| HS7C_MOUSE Heat shock cognate 71 kDa protein | | 123651 |
| hypothetical protein 4932412H11 | | 26325921 |
| integrin alpha 2; integrin alpha 2 (Cd49b); VLA-2 receptor, alpha 2 sub | | 6680478 |
| kinase D-interacting substance of 220 kDa | | 38049418 |
| Kinesin-like 6 | | 13905108 |
| laminin, beta 2; Laminin S | | 31982223 |
| Map3k4 protein | | 37590139 |

TABLE 5-continued

PROTEINS WITH ALTERATIONS IN PHOSPHORYLATION

| PROTEIN | HUMAN GI # | MOUSE GI# |
|---|---|---|
| mKIAA1565 protein | | 37360452 |
| Nitrogen fixation cluster-like | | 29476869 |
| olfactory receptor GA_x6K02T2PBJ9-6773690-6774628 | | 32057602 |
| phakinin, CP49 | | 17977856 |
| PSD3_MOUSE 26S proteasome non-ATPase regulatory subunit 3 (26S proteasome reg | | 19856169 |
| RIKEN cDNA 4833420I20 | | 17390408 |
| RIKEN cDNA 4930578C19 | | 30424860 |
| RIKEN cDNA 4933424A10 gene | | 28893379 |
| RIKEN cDNA 6030404K05 gene | | 30425216 |
| RIKEN cDNA 9030623C06 | | 34980904 |
| RIKEN cDNA A030005L19 | | 13386450 |
| RIKEN cDNA A930040G15 | | 19527136 |
| RIKEN cDNA C130068M19 gene | | 38073604 |
| RIKEN cDNA C730027J19 gene | | 30520215 |
| RIKEN cDNA F830010I22 gene | | 38091563 |
| Sema domain, immunoglobulin domain (Ig), and GPI membrane anchor, (semap | | 37046950 |
| SH3-domain GRB2-like 2 | | 17390906 |
| similar to 14-3-3 protein sigma | | 38089318 |
| similar to actin, gamma, cytoplasmic | | 38089775 |
| similar to cytoplasmic beta-actin | | 38089227 |
| similar to fibrous sheath-interacting protein 2 | | 38074908 |
| similar to integrin alpha 6 | | 38090030 |
| similar to ribosomal protein L31 | | 38085230 |
| solute carrier family 6 (neurotransmitter transporter, creatine), memb | | 19527208 |
| T-box 1 | | 20891977 |
| trypsinogen 16 | | 16716569 |
| Tubulin, alpha 2 | | 12805487 |
| uncoupling protein 2, mitochondrial | | 31543920 |
| Unknown (protein for MGC: 66590) | | 38348540 |
| Unknown (protein for MGC: 69991) | | 38328337 |
| Unknown (protein for MGC: 74310) | | 38174349 |
| unnamed protein product | | 26335149 |
| unnamed protein product | | 1333921 |
| unnamed protein product | | 26351281 |
| unnamed protein product | | 1333921 |

Example 2

Differential Expression of Activin Receptor-Like Kinase 1 (ALK1)

The activin receptor-like kinase 1 (ALK1), a TGF-betal type I receptor, plays an inhibitory role in angiogenesis and vascular development. Mutations of ALK1 gene are linked to human type II hereditary hemorrhagic telangiectasia. Our purpose was to develop a mouse model to study the differential expression of proteins during the phase of Hyaloid Vascular System (HVS) regression and determine the role of ALK1 in this model.

Materials and Methods: Thirty-two newborn C57BL/6 mice were sacrificed on post-gestational days 1 (n=20 eyes), 4 (n=20 eyes), 8 (n=12 eyes), and 16 (n=12 eyes). The lens, the Pupillary Membrane (PM), the Tunica Vasculosa Lentis (TVL) and the primary vitreous containing the Vasa Hyaloidea Propria (VHP) were isolated. Proteins were extracted from each specimen, loaded onto nonlinear immobilized pH gradient (IPG) gel strips, and separated by isoelectric points and molecular weights. Protein expression profile at each time point was compared using the Phoretix 2D image analysis software. Proteins from differentially expressed protein spots were isolated and identified using Mass Spectrometry (MS). Immunohistochemistry was performed to determine the expression of ALK1 during the HVS regression phase.

Results: The generated protein expression maps showed reproducible separation of the protein spots on the 2 Dimension Electrophoresis gels. Up to 1400 proteins spots were detected per gel. Progressive decrease in the number and intensity of the protein spots occurred from P1 to P 16, particularly in the area corresponding to pI 4-7 and $M_r$30 -90 kDa. Twenty protein spots in the P16 gels were not present in the P1 gels.

MS revealed 39 differentially expressed proteins (PP16-1 to 39) in the P16 specimens (Table 1). ALK1 was identified as PP16-31 (spot n° 17). The warping of P16 with P1, P4 and P8 showed the presence of this spot only in P4 and P8. Immunohistochemistry of the cornea, PM, and TVL using anti ALK1 antibody confirmed the presence of ALK1 in the TVL at P4 and P16.

Conclusion: The synthesis or degradation of one or more proteins, present at P16 (PP16-1 to 39), may be related to the regression of HVS in the mouse. Identification of ALK1 by proteomic analysis and immunohistochemistry in this model suggests that the TGF-betal pathway may be involved in this process.

Example 3

Progressive Regression of HVS in the Mouse and the Differential Protein Expression Profile A time course experiment was designed to examine the changes in protein expression at P1 and P16 throughout the HVS regression process. As this is the first reported application of proteomic analysis on HVS regression, several conditions for tissue selection and preparation were developed and optimized to obtain clean specimens of the lens and vitreous for 2-DE gels.

Mouse Anterior Tissue Preparation for 2-DE Gels

For the protein extraction and ALK1 immunolocalization studies, newborn mice were sacrificed on post-natal days 1, 4 and 16. Using a dry ice bed, frozen mouse eyes were scraped with a blade (Beaver #15) to remove the cornea, conjunctiva, sclera, ciliary body, uvea, and retina, leaving the lens surrounded by the PM, TVL, and primary vitreous (containing VHP). The dry ice bed was used to prevent warming of the specimen, tissue melting, and subsequent protein denaturation. Samples of P1, P4 and P16 were pooled and independently solubilized in 250 µl of total protein extraction buffer 7 M urea, 2 M thiourea, 1% (w/v) ASB-14 detergent, 40 mM Tris base, 0.001% bromophenol blue, 20% carrier ampholyte (Biorad Laboratories, Hercules, Calif.) and 2 µl of 200 mM tributylphosphine by mechanically homogenizing them with an electrical tissue homogenizer for 5 min on ice. The homogenates of the protein extracts were cleared by centrifugation for 20 min at 14,000 rpm and 4° C. to remove particulates. Protein concentration of the supernatants was determined by protein assay (Biorad Laboratories).

Two-dimensional Electrophoresis, Image analysis and Protein Identification

Three samples per each post-gestational day were loaded onto nonlinear, immobilized pH gradient (IPG) gel strips (7 cm, pH 3-10), subjected to isoelectric focusing with a programmed voltage gradient at 8,000 V for 5 hours, and rehydrated overnight with rehydration/sample buffer (Biorad Laboratories). IPG strips were equilibrated with buffer containing 6 M urea, 50 mM Tris (pH 8.8), 30% glycerol, 2% SDS (sodium dodecyl sulfate), and 0.001% bromophenol blue containing 2% DTT (dithiothreitol) or 2.5% iodoacetamide. Following equilibration, second-dimension separation was performed on 4-20% SDS-PAGE (SDS-polyacrylamide gel electrophoresis) gels (Biorad Laboratories) with the first-dimension IPG strip embedded in 0.5% agarose at the top. After electrophoresis, the proteins on the gel were fixed in 10% acetic acid and 20% methanol for 1 hour and then stained with SYPRO™ Ruby (Biorad Laboratories). Images of the 2-DE (two-dimensional electrophoresis) gels were captured with Molecular Imager FX Pro Plus multi-imager system and the protein expression profiles at each time point were compared, in triplicate, using the Phoretix 2D image analysis software. Protein spots present in P16 with expression level two- to ten-fold greater than P1 were considered for protein identification. The statistical significance of changes was evaluated using Phoretix 2D software.

Gel bands (differentially expressed proteins) from 2-DE gels were excised, minced into approximate 1 mm$^3$ pieces with a sterile razor blade of the Xcise technology platform from Proteome system, alkylated, and digested with trypsin (Promega, Madison, Wis.). Peptides were resuspended in 50% acetonitrile with 1% formic acid solution and subjected to nano-LC ESI IT MS/MS analysis. A Surveyor LC pump (Thermo Electron, San Jose, Calif.) with a C18 trapping column (300 µm i.d.×1 mm, Dionex, Sunnyvale, Calif.) and a reversed-phase column 75 µm i.d.×15 cm (Magic C18AQ, 3 µm) was used for nano-LC experiments. An LCQ Deca XP plus ESI mass spectrometer (Thermo Electron, San Jose, Calif.) was used for all the experiments.

MS/MS data-dependent acquisition followed by database searching with SEQUEST (BioWorks 3.1, Thermo Electron, San Jose, Calif.) allowed protein identification. Fully tryptic peptides were matched with SEQUEST at a delta correlation (ÄCn) of greater than 0.08 and correlation (Xcorr) greater than 1.9, 2.2, and 3.5 for charged states of +1, +2, and +3, respectively. Peptide mass fingerprints (PMFs) were searched for matches with the virtually generated tryptic protein masses of the NCBInr mouse protein sequence database (available at ncbi.nml.nih.gov). All databases were provided in the public domain by the host institutions. Proteins were noted as differentially expressed if they could not be located at the corresponding position on the 2-DE gel of the other time point.

Protein expression maps were generated in triplicate for each time point, obtaining a reproducible separation of the protein spots on the 2-DE gels. Up to 1400 protein spots could be detected in each gel with the Phoretix 2D image analysis software (FIG. 1A). This software allows the possibility to warp different gel images to improve the quality of the protein spot matching between the gels and allow an easy detection of the differences among the gels. The 2-DE gels were analyzed, and a progressive decrease in the number and intensity of the protein spots from P1 to P16 was observed, particularly of the migrated proteins in the area corresponding to pI 4-7 and $M_w$ 30-90 kDa (FIG. 1B-C).

However, the warping of the 2-D gel images of P1 with P16 revealed the presence of a small number of protein spots for which expression level in P16 was two to ten-fold greater than P1. Twenty protein spots were analyzed using mass spectrometry analysis. some of these identified proteins displayed slightly different molecular weights and pIs, suggesting the presence of different isoforms or posttranslational modifications. eighteen differentially expressed proteins were identified; two additional proteins were unclassified and 15 were unknown. ALK1 was identified as spot #17.

TABLE 6

PROTEINS WITH DIFFERENTIAL EXPRESSION AT POST-GESTATIONAL DAY 16

| SPOT # | PROTEIN NAME | MOUSE GENE BANK # | HUMAN HOMOLOG GENE BANK # |
|---|---|---|---|
| 1 | RAD50 homolog | 6679609 | 19924130 |
| 2 | Olfactory receptor GA_x6K02T2PBJ9-6773690-6774628 | 32057602 | 41200972 |
| 3 | Cofilin 1, non-muscle | 28374265 | 116848 |
| 4 | Guanine nucleotide-binding protein, β-1 subunit | 15341782 | 20357526 |
| 5 | Protein kinase, cAMP dependent regulatory, type I β | 15030299 | 1346362 |
| 6 | α enolase (2-phospho-D-glycerate hydro-lyase) (non-neural enolase) | 13637776 | 119339 |
| 7 | Cathepsin 3 precursor | 21450788 | 30582658 |
| 8 | Unclassified | | |
| 9 | Knsl7 protein | 26095143 | Knsl7 |
| 10 | F-box/LRR-repeat protein 3B (F-box and leucine-rich repeat protein) | 37537783 | 16306584 |
| 11 | Enolase 3, β muscle | 15488630 | 16554592 |
| 12 | Albumin 1 | 19353306 | 113576 |
| 13 | Heat shock cognate 71 kDa protein | 123651 | 123648 |
| 14 | Fatty acid binding protein 5, epidermal; keratinocyte lipid binding protein | 6754450 | 4557581 |
| 15 | Vimentin | 31982755 | 57471648 |
| 16 | Tubulin, β 2 | 33416314 | 4507729 |
| 17 | ALK1 protein | 6752957 | 4557243 |
| 18 | CRAA_MOUSE α crystallin A chain, major component | 117369 | 1706112 |
| 19 | Crystallin, β A4 | 33989574 | 4503059 |
| 20 | Unclassified | | |

Example 4

Immunolocalization of ALK1 in the TVL by Confocal Microscopy

To investigate whether ALK1 is expressed in TVL during mouse development, mouse eyes at P1, P4 and P16 were immunostained with anti-ALK1 antibody.

ALK1 Immunolocalization by Confocal Microscopy

Mouse eyes harvested at P1, P4, and P16 were embedded in optimal cutting temperature (OCT) compound (Miles, Elkhart, Ind.), frozen in liquid nitrogen, cryostat sectioned, and fixed in acetone for 10 min. After blocking with 1% bovine serum albumin (BSA) (Sigma Chemical Co., St. Louis, Mo.) for 30 min, the sections were incubated for 1 hour with rabbit anti-ALK1 polyclonal antibody (courtesy of Dr. D. A. Marchuck, University of North Carolina) at a concentration of 1:200. A secondary antibody used was fluorescein-conjugated, affinity-purified anti-rabbit IgG antibody (Jackson ImmunoResearch Laboratories, West Grove, Pa.) at a concentration of 1:400. Negative controls were prepared in the same manner, with 1% BSA without primary antibody. Immunostained sections were viewed with a Leica TCS SP2 CLSM confocal laser scanning microscope (Leica, Heidelberg, Germany).

Results

The confocal immunohistochemical staining demonstrated that ALK1 is localized in the endothelial cells of the TVL at P1, P4 and P16.

Example 5

Naked pEF-ALK1 DNA Blocked bFGF Induced Corneal NV in Vivo

Naked DNA has been effectively used for the delivery of DNA into mouse corneas. To determine whether ALK1 can inhibit bFGF-induced corneal NV (neovascularization), mouse corneas were injected with naked DNAs of pEF (vector) and pEF-ALK1.

Plasmid Construction and Corneal Naked DNA Injection pYX-Asc-ALK1 cDNA was purchased from ATCC (Manassas, Va.). Plasmids were purified using a Qiagen kit (Valencia, Calif.) according to the manufacturer's instructions. The mouse ALK1 DNA was sequenced and subcloned into pEF expression vector. An Elongation Factor 1 alpha promoter (pEF; Kim et al., Gene. 1990 Jul. 16;91(2):217-23) was used to drive the expression of the ALK1 gene. Mouse corneas received a DNA injection of 5 µl of pEF-ALK1 (400 ng/µl) or an injection of 5 µl of vector (400 ng/µl). An antibiotic ophthalmic ointment was used after surgery.

bFGF Pellet Preparation and Corneal Micropocket Assay

Pellets were made of the slow-release polymer Hydron (polyhydroxyethyl-methacrylate), which contained a combination of 45 ng/pellet of sucralfate (Sigma) and 120 ng/pellet of bFGF (R&D Systems, Minneapolis, Mn.), as previously described by Kenyon et al., Invest Ophthalmol Vis Sci 37, 1625-1632 (1996).

Briefly, a suspension of sterile saline containing the appropriate amount of recombinant bFGF and sucralfate was made and concentrated using a speed-vacuum for 8 minutes. To this suspension, 10 µl of 12% Hydron in ethanol was added. The suspension was then deposited onto a sterilized nylon mesh (LAB Pak, Sefar America, Depew, N.Y.) and embedded between the fibers. The resulting grid of 10 mm×10 mm squares was allowed to dry on a sterile Petri dish for 60 min. The fibers of the mesh were pulled apart under a microscope and, among the approximately 100 pellets produced, 30 to 40 uniformly-sized pellets of 0.4×0.4×0.2 mm were selected for implantation. All procedures were performed under sterile conditions.

Three days after the naked DNA injections, corneal micropockets were created with a modified von Graefe knife in C57BL/6 mice. Hydron pellets containing 120 ng of human basic FGF were implanted into the corneal pockets.

Measurement of Corneal Neovascularization

The corneas were routinely examined and photographed in five positions: en face, superior, inferior, nasal, and temporal with a slit lamp biomicroscope (Nikon FS-2, Tokyo, Japan) on days 1, 4, 7, and 14 post-pellet implantation. The photographs were digitized and the images were resolved at 300 pixels/inch and analyzed with the NIH ImageJ image program (NIH, Bethesda, Md.). NIH ImageJ program was used to calculate the area of corneal neovascularization areas. Statistical analysis was performed with the student T-test.

Results

The ALK1 plus pellet group (FIG. 2M-P) showed no evidence of corneal NV at any time point after pellet implantation. The group receiving vector control plus pellets (FIG. 2I-L) began to develop corneal NV at day 4, and the new vessels continued to grow toward the pellet area at days 7 and 14. The area occupied by neovascularization in the ALK1 treated mice was 0.58 mm$^2$ and 0.47 mm$^2$ at days 7 and 14 after bFGF pellet implantation, respectively (FIG. 2O-P). This was significantly less than the vector treated mice 3.14 mm$^2$ ($p=0.001$) and 3.33 mm$^2$ ($p=0.001$) at 7 and 14 days after bFGF pellet implantation, respectively (FIG. 2K-L). The no-pellet control groups [ALK1 naked DNA (FIG. 2E-H) and vector naked DNA (FIG. 2A-D)] did not induce corneal NV.

These results demonstrate that injection of naked pEF-ALK1 DNA blocked bFGF induced corneal NV.

ADDITIONAL REFERENCES

1. Goumans and Mummery, Int. J. Dev. Biol. 44, 253-265 (2000).
2. Goumans et al., Trends. Cardiovasc. Med. 13, 301-307 (2003).
3. Pepper, Cytokine Growth Factor. Rev. 8, 21-43 (1997).
4. Lamouille et al., Blood 100, 4495-4501 (2002).
5. Roman et al., Development 129, 3009-3019 (2002).
6. Lebrin et al., Cardiovasc. Res. 65, 599-608 (2005).
7. Lebrin et al., EMBO. J. 23, 4018-4028 (2004).
8. Gabison et al., Exp. Eye. Res. 78, 579-589 (2004).
9. Murthy et al., Invest. Ophthalmol. Vis. Sci. 44, 1837-1842 (2003).
10. Chang et al., Curr. Opin. Ophthalmol. 12, 242-249 (2001).
11. Dawson et al., Science 285, 245-248 (1999).
12. Chang et al., FEBS. Lett. 579, 3601-3606 (2005).
13. Urness et al., Nat. Genet. 26, 328-331 (2000).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for inhibiting corneal neovascularization in a human subject, the method comprising:
   administering to the subject a therapeutically effective amount of a therapeutic composition comprising a polynucleotide comprising nucleotides 346-1791 of SEQ ID NO:2,
   thereby inhibiting corneal neovascularization in the subject.

2. The method of claim 1, wherein the administering is by topical or parenteral administration into the eye.

3. The method of claim 2, wherein the administering is by local injection into or near the cornea.

4. The method of claim 1, wherein the therapeutic composition comprises naked DNA comprising a polynucleotide comprising nucleotides 346-1791 of SEQ ED NO:2.

5. The method of claim 1, wherein the polynucleotide encodes a polypeptide comprising amino acids 22-503 of SEQ ID NO:1.

6. The method of claim 4, wherein the naked DNA is administered into the eye of the subject.

7. The method of claim 6, wherein the naked DNA is injected into the eye of the subject using peribulbar or intravitreal injection.

8. The method of claim 4, wherein the polynucleotide encodes a polypeptide comprising amino acids 22-503 of SEQ ID NO:1.

9. The method of claim 1, further comprising, before step (i), selecting a subject with corneal neovascularization.

10. A method for inhibiting corneal neovascularization in a human subject, the method comprising:
    administering to the subject a therapeutically effective amount of a therapeutic composition comprising a polynucleotide encoding a polypeptide comprising amino acids 22-503 of SEQ ID NO:1, thereby inhibiting corneal neovascularization in the subject.

11. The method of claim 10, wherein the administering is by topical or parenteral administration into the eye.

12. The method of claim 11, wherein the administering is by local injection into or near the cornea.

13. The method of claim 10, wherein the therapeutic composition comprises naked DNA comprising a polynucleotide encoding a polypeptide comprising amino acids 22-503 of SEQ ID NO:1.

14. The method of claim 13, wherein the naked DNA is administered into the eye of the subject.

15. The method of claim 14, wherein the naked DNA is injected into the eye of the subject using peribulbar or intravitreal injection.

16. The method of claim 10, further comprising selecting a subject with corneal neovascularization.

* * * * *

SEQUENCE LISTING

<160> NUMBER OF SEQ ID NOS: 2

<210> SEQ ID NO 1
<211> LENGTH: 503
<212> TYPE: PRT
<213> ORGANISM: Homo sapiens

<400> SEQUENCE: 1

Met Thr Leu Gly Ser Pro Arg Lys Gly Leu Leu Met Leu Leu Met Ala

-continued

```
  1               5                  10                 15
Leu Val Thr Gln Gly Asp Pro Val Lys Pro Ser Arg Gly Pro Leu Val
             20                  25                 30

Thr Cys Thr Cys Glu Ser Pro His Cys Lys Gly Pro Thr Cys Arg Gly
             35                  40                 45

Ala Trp Cys Thr Val Val Leu Val Arg Glu Glu Gly Arg His Pro Gln
 50                  55                 60

Glu His Arg Gly Cys Gly Asn Leu His Arg Glu Leu Cys Arg Gly Arg
 65                  70                 75                 80

Pro Thr Glu Phe Val Asn His Tyr Cys Asp Ser His Leu Cys Asn
             85                  90                 95

His Asn Val Ser Leu Val Leu Glu Ala Thr Gln Pro Ser Glu Gln
             100                 105                110

Pro Gly Thr Asp Gly Gln Leu Ala Leu Ile Leu Gly Pro Val Leu Ala
             115                 120                125

Leu Leu Ala Leu Val Ala Leu Gly Val Leu Gly Leu Trp His Val Arg
 130                 135                140

Arg Arg Gln Glu Lys Gln Arg Gly Leu His Ser Glu Leu Gly Glu Ser
145                  150                155                160

Ser Leu Ile Leu Lys Ala Ser Glu Gln Gly Asp Thr Met Leu Gly Asp
             165                 170                175

Leu Leu Asp Ser Asp Cys Thr Thr Gly Ser Gly Ser Gly Leu Pro Phe
             180                 185                190

Leu Val Gln Arg Thr Val Ala Arg Gln Val Ala Leu Val Glu Cys Val
             195                 200                205

Gly Lys Gly Arg Tyr Gly Glu Val Trp Arg Gly Leu Trp His Gly Glu
             210                 215                220

Ser Val Ala Val Lys Ile Phe Ser Ser Arg Asp Glu Gln Ser Trp Phe
225                  230                235                240

Arg Glu Thr Glu Ile Tyr Asn Thr Val Leu Leu Arg His Asp Asn Ile
             245                 250                255

Leu Gly Phe Ile Ala Ser Asp Met Thr Ser Arg Asn Ser Ser Thr Gln
             260                 265                270

Leu Trp Leu Ile Thr His Tyr His Glu His Gly Ser Leu Tyr Asp Phe
             275                 280                285

Leu Gln Arg Gln Thr Leu Glu Pro His Leu Ala Leu Arg Leu Ala Val
             290                 295                300

Ser Ala Ala Cys Gly Leu Ala His Leu His Val Glu Ile Phe Gly Thr
305                  310                315                320

Gln Gly Lys Pro Ala Ile Ala His Arg Asp Phe Lys Ser Arg Asn Val
             325                 330                335

Leu Val Lys Ser Asn Leu Gln Cys Cys Ile Ala Asp Leu Gly Leu Ala
             340                 345                350

Val Met His Ser Gln Gly Ser Asp Tyr Leu Asp Ile Gly Asn Asn Pro
             355                 360                365

Arg Val Gly Thr Lys Arg Tyr Met Ala Pro Glu Val Leu Asp Glu Gln
 370                 375                380

Ile Arg Thr Asp Cys Phe Glu Ser Tyr Lys Trp Thr Asp Ile Trp Ala
385                  390                395                400

Phe Gly Leu Val Leu Trp Glu Ile Ala Arg Arg Thr Ile Val Asn Gly
             405                 410                415

Ile Val Glu Asp Tyr Arg Pro Pro Phe Tyr Asp Val Val Pro Asn Asp
             420                 425                430
```

```
Pro Ser Phe Glu Asp Met Lys Lys Val Val Cys Val Asp Gln Gln Thr
        435                 440                 445

Pro Thr Ile Pro Asn Arg Leu Ala Ala Asp Pro Val Leu Ser Gly Leu
    450                 455                 460

Ala Gln Met Met Arg Glu Cys Trp Tyr Pro Asn Pro Ser Ala Arg Leu
465                 470                 475                 480

Thr Ala Leu Arg Ile Lys Lys Thr Leu Gln Lys Ile Ser Asn Ser Pro
                485                 490                 495

Glu Lys Pro Lys Val Ile Gln
            500

<210> SEQ ID NO 2
<211> LENGTH: 1970
<212> TYPE: DNA
<213> ORGANISM: Homo sapiens

<400> SEQUENCE: 2
aggaaacggt ttattaggag ggagtggtgg agctgggcca ggcaggaaga cgctggaata      60
agaaacattt ttgctccagc ccccatccca gtcccgggag gctgccgcgc cagctgcgcc     120
gagcgagccc ctcccccggct ccagcccggt ccggggccgc gccggacccc agcccgccgt    180
ccagcgctgg cggtgcaact gcggccgcgc ggtggagggg aggtggcccc ggtccgccga    240
aggctagcgc cccgccaccc gcagagcggg cccagaggga ccatgacctt gggctccccc    300
aggaaaggcc ttctgatgct gctgatggcc ttggtgaccc aggagaccc tgtgaagccg    360 tctcggggcc cgctggtgac ctgcacgtgt gagagcccac attgcaaggg gcctacctgc    420
cggggggcct ggtgcacagt agtgctggtg cgggaggagg ggaggcaccc ccaggaacat    480
cggggctgcg ggaacttgca cagggagctc tgcagggggc gccccaccga gttcgtcaac    540
cactactgct gcgacagcca cctctgcaac acaacgtgt ccctggtgct ggaggccacc    600
caacctcctt cggagcagcc gggaacagat ggccagctgg ccctgatcct gggccccgtg    660
ctggccttgc tggccctggt ggccctgggt gtcctgggcc tgtggcatgt ccgacggagg    720
caggagaagc agcgtggcct gcacagcgag ctggagagt ccagtctcat cctgaaagca    780
tctgagcagg gcgacacgat gttggggac ctcctggaca gtgactgcac cacagggagt    840
ggctcagggc tccccttcct ggtgcagagg acagtggcac ggcaggttgc cttggtggag    900
tgtgtgggaa aaggccgcta tggcgaagtg tggcggggct tgtggcacgg tgagagtgtg    960
gccgtcaaga tcttctcctc gagggatgaa cagtcctggt tccgggagac tgagatctat   1020
aacacagtat tgctcagaca cgacaacatc ctaggcttca tcgcctcaga catgacctcc   1080
cgcaactcga gcacgcagct gtggctcatc acgcactacc acgagcacgg ctccctctac   1140
gactttctgc agagacagac gctggagccc atctggctc tgaggctagc tgtgtccgcg   1200
gcatgcggcc tggcgcacct gcacgtggag atcttcggta cacagggcaa accagccatt   1260
gcccaccgcg acttcaagag ccgcaatgtg ctggtcaaga gcaacctgca gtgttgcatc   1320
gccgacctgg gctggctgt gatgcactca cagggcagcg attacctgga tcggcaac    1380 aacccgagag tgggcaccaa gcggtacatg gcacccgagg tgctggacga gcagatccgc   1440
acggactgct ttgagtccta caagtggact gacatctggg cctttggcct ggtgctgtgg   1500
gagattgccc gccggaccat cgtgaatggc atcgtggagg actatagacc acccttctat   1560
gatgtggtgc caatgaccc cagctttgag gacatgaaga aggtggtgtg tgtggatcag   1620
cagaccccca ccatccctaa ccggctggct gcagacccgg tcctctcagg cctagctcag   1680
```

```
atgatgcggg agtgctggta cccaaacccc tctgcccgac tcaccgcgct gcggatcaag    1740
aagacactac aaaaaattag caacagtcca gagaagccta aagtgattca atagcccagg    1800
agcacctgat tcctttctgc ctgcaggggg ctggggggt ggggggcagt ggatggtgcc    1860
ctatctgggt agaggtagtg tgagtgtggt gtgtgctggg gatgggcagc tgcgcctgcc    1920
tgctcggccc ccagcccacc cagccaaaaa tacagctggg ctgaaacctg              1970
```